US011312675B2

(12) United States Patent
Giaffreda et al.

(10) Patent No.: US 11,312,675 B2
(45) Date of Patent: *Apr. 26, 2022

(54) CRYSTALLINE POLYMORPHS OF 1,6-DIBROMO-1,6-DIDEOXY-DULCITOL

(71) Applicant: Targent, LLC, Princeton, NJ (US)

(72) Inventors: Stefano Luca Giaffreda, Bologna (IT); Elena Dichiarante, Bologna (IT)

(73) Assignee: Eleison Pharmaceuticals, LLC, Princeton, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/930,193

(22) Filed: May 12, 2020

(65) Prior Publication Data

US 2020/0270193 A1 Aug. 27, 2020

Related U.S. Application Data

(63) Continuation of application No. 15/736,909, filed as application No. PCT/US2016/037531 on Jun. 15, 2016, now Pat. No. 10,654,783.

(60) Provisional application No. 62/325,194, filed on Apr. 20, 2016, provisional application No. 62/180,256, filed on Jun. 16, 2015.

(51) Int. Cl.
| | | |
|---|---|---|
| A61K 31/047 | (2006.01) | |
| A61K 47/10 | (2017.01) | |
| A61K 47/60 | (2017.01) | |
| C07C 31/42 | (2006.01) | |
| C07C 29/78 | (2006.01) | |
| C07C 29/76 | (2006.01) | |
| A61P 35/00 | (2006.01) | |
| A61K 45/06 | (2006.01) | |
| A61N 5/10 | (2006.01) | |
| C12Q 1/6886 | (2018.01) | |

(52) U.S. Cl.
CPC ............ *C07C 31/42* (2013.01); *A61K 31/047* (2013.01); *A61K 45/06* (2013.01); *A61K 47/10* (2013.01); *A61K 47/60* (2017.08); *A61N 5/10* (2013.01); *A61P 35/00* (2018.01); *C07C 29/76* (2013.01); *C12Q 1/6886* (2013.01); *C07B 2200/13* (2013.01); *C12Q 2600/106* (2013.01)

(58) Field of Classification Search
CPC ...... A61K 31/047; A61K 47/10; A61K 47/60; C07C 31/42; C07C 29/78; C07C 29/76; A61P 35/00
USPC .................. 514/738; 568/853, 854
See application file for complete search history.

(56) References Cited

U.S. PATENT DOCUMENTS

| | | | | |
|---|---|---|---|---|
| 3,993,781 | A | * | 11/1976 | Horvath nee Lengyel ................. A61K 31/70 514/738 |
| 10,654,783 | B2 | * | 5/2020 | Giaffreda ............. C12Q 1/6886 |

FOREIGN PATENT DOCUMENTS

WO 2013110058 A2 7/2013

OTHER PUBLICATIONS

B. Kellner, et al, "Pharmacology of 1,6-Dibromo-1,6-Dideoxy-Dulcitol and its Cytostatic Effect on Transplantable Tumours," from the Research Institute of Oncopathology, Budapest (Hungary), 1967, pp. 1037-1043.
Bauer et al., "Ritonavir: An Extraordinary Example of Conformational Polymorphism", Pharmaceutical Research, vol. 18, No. 6, pp. 859-866, (2001).
EPO Office Action dated Apr. 26, 2019 received in corresponding EP Application 16 732 851.7.
International Preliminary Report on Patentability dated Dec. 19, 2017 received in PCT/US2016/037531.
International Search Report and Written Opinion dated Sep. 14, 2016 and received in PCT/US2016/037531.
K. Simon, "The Crystal and Molecular Structure of Dibromodulcitol C6H1204Br2 and Dichlorodulcitol C6H1204C12," Acta Cryst. B27, vol. B27, No. 282, Jan. 1, 1967, pp. 754-806 (XP55299518).
Kellner et al. "1,6-Dibromo-1,6-Dideoxy-Dulcitol: A New Antitumoral Agent," Nature pp. 402-403 (1967).
L. Dobrosy, "The Hematological Effect of a New Cytostatic: 1,6-Dibromo-1,6-Dideoxy-Dulcitol (DBD) In Animal Experiments," Neoplasma, vol. 16, No. 1, Oncopathological Research Institute, Budapest, Hungary, 1969, pp. 33-41.
Priority Document GB 940.
T. Valyi-Nagy, "Pharmaco-Biochemical Studies on Cytotoxic Polyol Derivates I. Effects of 1-6-Dibromo-1-6-Dideoxy-Dulcitol on Sensitive, Resistant and Refractor Tumours," Europ. J. Cancer, vol. 5, 1969, pp. 403-414.
Vasudev et al., "Crystal Structures of a New Polymorphic Form of Gabapentin Monohydrate and the E and Z Isomers of 4-Tertiarybutylgabapentin", Chem Biol Drug Des, vol. 73, pp. 83-96, (2009).
Yu et al., "Polymorphism in Molecular Solids: An Extraordinary System of Red, Orange, and Yellow Crystals", Accounts of Chemical Research, vol. 43, No. 9, pp. 1257-1266, (2010).

\* cited by examiner

*Primary Examiner* — Joseph R Kosack
*Assistant Examiner* — Sagar Patel
(74) *Attorney, Agent, or Firm* — Michele M. Wales; InHouse Patent Counsel, LLC

(57) ABSTRACT

Described herein are polymorphic forms of 1,6-dibromo-1,6-dideoxy-dulcitol (dibromo dulcitol or DBD), which is a known antitumor agent. Also described are methods of making these new crystalline polymorphic forms as well as methods of using these polymorphic forms to treat cancer.

31 Claims, 9 Drawing Sheets

CRYSTALLINE POLYMORPHS OF 1,6-DIBROMO-1,6-DIDEOXY-DULCITOL

CROSS-REFERENCE TO RELATED APPLICATIONS

This application is a Continuation Application of U.S. Ser. No. 15/736,909, filed Dec. 15, 2017, which is a § 371 National Stage Application of PCT/US16/37531 filed on Jun. 15, 2016, which claims priority to U.S. Provisional Applications 62/180,256 filed on Jun. 16, 2015 and US 62/325,194 filed on Apr. 20, 2016. All of these documents are hereby incorporated by reference in their entirety.

FIELD OF THE INVENTION

Described herein are polymorphic forms of 1,6-dibromo-1,6-dideoxy-dulcitol (dibromo dulcitol or DBD), which is a known antitumor agent. Also described are methods of making these new crystalline polymorphic forms as well as methods of using these polymorphic forms to treat cancer.

INTRODUCTION

Cancer is the second leading cause of death in the United States, exceeded only by heart disease. Despite recent advances in cancer diagnosis and treatment, surgery and radiotherapy may be curative if a cancer is found early, but current drug therapies for metastatic disease are mostly palliative and seldom offer a long-term cure. Even with new chemotherapies entering the market, the need continues for new drugs effective in monotherapy or in combination with existing agents as first line therapy, and as second and third line therapies in treatment of resistant tumors.

One example of a potential chemotherapeutic used to treat cancer is 1,6-dibromo-1,6-dideoxy-dulcitol (dibromo dulcitol or DBD). The crystal structure of DBD was first published by Simon and Sasvari in *Acta. Cryst.* (1971) B27, 806-815. Kellner et al., reported that DBD had a selective a vigorous antitumor effect. Kellner et al., "1,6-*Dibromo*-1,6-*Dideoxy-Dulcitol: A New Antitumoral Agent*." Nature (1967) 28: 213 (5074):402-3. However, in these studies, DBD was prepared by treating dulcitol with aqueous hydrobromic acid saturated with gaseous hydrogen bromide at temperatures less than 0° C. This process is no longer considered a safe method of making DBD. Moreover, it was reported in the literature that DBD was poorly soluble.

The present invention addresses the continued need to improve and develop new cancer treatments that are safe to manufacture.

SUMMARY OF THE INVENTION

This summary is provided to introduce a selection of concepts in a simplified form that are further described below in the Detailed Description.

Described herein are crystalline polymorphs of 1,6-dibromo-1,6-dideoxy-dulcitol, which has the following structure:

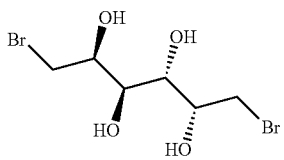 [SMILES: O[C@H]([C@H](O)[C@@H](O)CBr)[C@H](O)CBr]

DBD has a molecular weight of 307.98 g/mol and the molecular formula $C_6H_{12}Br_2O_4$.

In one aspect described herein are crystalline polymorphs of 1,6-dibromo-1,6-dideoxy-dulcitol characterized by peaks at 19.59° (100,00) and 24.380° (79,52) and 31.260° (8,32) and 34.500° (25,56) and 34.810° (22,83) and 39.260° (23, 63) at 2θ±0.1°. In further embodiments, such a crystalline polymorph is further characterized by at least two peaks selected from 19.59° (100,00) and 24.380° (79,52) and 31.260° (8,32) and 34.500° (25,56) and 34.810° (22,83) and 39.260° (23,63) at 2θ±0.10. In further embodiments, such a crystalline polymorph is further characterized by at least three peaks selected from 19.59° (100,00) and 24.380° (79,52) and 31.260° (8,32) and 34.500° (25,56) and 34.810° (22,83) and 39.260 (23,63) at 2θ±0.10. In further embodiments, such a crystalline polymorph is further characterized by at least four peaks selected from 19.59° (100,00) and 24.380° (79,52) and 31.260° (8,32) and 34.500° (25,56) and 34.810° (22,83) and 39.260° (23,63) at 2θ±0.1°. In further embodiments, such a crystalline polymorph is further characterized by at least five peaks selected from 19.59° (100,00) and 24.380° (79,52) and 31.260° (8,32) and 34.500° (25,56) and 34.810° (22,83) and 39.260° (23,63) at 2θ±0.10.

In yet further embodiments, the crystalline polymorph exhibits an x-ray powder diffraction pattern substantially the same as the x-ray powder diffraction pattern shown in FIG. 1. In further embodiments, the crystalline polymorph exhibits an x-ray powder diffraction pattern substantially the same as the x-ray powder diffraction pattern shown in FIG. 2. In yet further embodiments, the crystalline polymorph exhibits an x-ray powder diffraction pattern substantially the same as the x-ray powder diffraction pattern described in Table 1. In yet further embodiments, the crystalline polymorph exhibits a beta angle of 96° as compared to the literature reported beta angle of 98°.

In a related aspect described herein are crystalline polymorphs of 1,6-dibromo-1,6-dideoxy-dulcitol, characterized by an endothermic point onset at about 184.4° C. and peak at approximately 191° C. as determined by differential scanning calorimetry. In a further embodiment, the crystalline polymorph is characterized by a differential scanning calorimetry pattern substantially the same as the differential scanning calorimetry pattern shown in FIG. 3 and/or FIG. 4.

Other aspects of the invention include solid pharmaceutical compositions comprising an effective amount of the crystalline polymorph characterized by the aforementioned diffraction patterns, an effective amount of the crystalline polymorph characterized by the aforementioned differential scanning calorimetry patterns, or an effective amount of the crystalline polymorph, as an active ingredient; and at least one excipient or carrier.

Also described herein are methods for treating cancer comprising administering an effective amount of the crystalline polymorph characterized by the aforementioned diffraction patterns, an effective amount of the crystalline polymorph characterized by the aforementioned differential scanning calorimetry patterns, or an effective amount of the crystalline polymorph.

In preferred embodiments, the cancer that is treated using the crystalline polymorph of DBD is an adenocarcinoma, sarcoma, skin cancer, melanoma, bladder cancer, brain cancer, breast cancer, uterine cancer, ovarian cancer, prostate cancer, lung cancer, colorectal cancer, cervical cancer, liver cancer, head and neck cancer, esophageal cancer, pancreas cancer, pancreatic ductal adenocarcinoma (PDA), renal cancer, stomach cancer, multiple myeloma or cerebral cancer. In even further embodiments, the crystalline polymorph described herein can be used to treat brain, head and neck, lymphoma, melanoma, breast, cervical, and other cancers of the central nervous system. In even further preferred embodiments, the crystalline polymorph described herein can be used to treat pediatric cancers, such as pediatric brain cancer and pediatric leukemia. Other preferred cancers that can be treated with the crystalline polymorph described herein include, pulmonary (e.g., non-small cell lung cancer), gastric, renal, ovarian, uterine, colonic and bladder carcinomas, as well as in brain tumors and sarcomas.

In other embodiments, the cancer that is treated using the crystalline polymorph of DBD or compositions thereof is a cancer that has metastasized to the brain, including but not limited to cancer originating from breast cancer, lung cancer, colon cancer, kidney cancer, pancreatic cancer, or malignant melanomas.

In other embodiments, the crystalline DBD polymorph or compositions thereof may be used in combination with other therapeutic treatments, such as radiation therapy. Radiation therapy may be administered using any radiation-delivering system, including gantry-based systems, robotic radiosurgery systems, subcutaneous implants, radioisotopes, etc.

In still other embodiments, the crystalline DBD polymorph can be formulated with polyethylene glycol (PEG) to form a PEGylated DBD polymorph composition. e.g., to alter absorption characteristics, to alter the therapeutic index of the crystalline DBD polymorph, etc., for administration to the patient.

In still other embodiments, the crystalline DBD polymorph can be administered in combination with molecules which block or inhibit cellular DNA-repair mechanisms, such as polyADP-ribose polymerase protein (PARP) inhibitors, alkylating agents, and so forth. PARP inhibitors include Olaparib, Talazoparib, MK-4827. BGB-290, 3-aminobenzamide, CEP 9722, Veliparib and Rucaparib. Alkylating agents include the following classes of compounds: mustard gas derivatives, nitrosoureas, thylenimines/methylmelamines, triazenes, sulfonates and metal salts. Specific examples of alkylating agents include: nitrogen mustards, such as mechlor-ethamine, cyclophosphamide, ifosfamide, melphalan, chlorambucil, and temozolomide; nitrosoureas, such as carmustine (BCNU), lomustine (CCNU), and semustine (methyl-CCNU); thylenimines/methylmelamines such as thriethylenemelamine (TEM), triethylene, thiophosphoramide (thiotepa), hexamethylmelamine (HMM, altretamine); alkyl sulfonates (including sulfonate esters) such as busulfan; triazines such as dacarbazine (DTIC); and metal salts such as carboplatin, cisplatin, and oxaliplatin.

Molecules that block DNA repair include molecules that block any of a variety of DNA repair pathways, including: molecules that block direct repair by inhibiting or depleting MGMT (e.g., temozolomide, $O^6$ benzylguanine, etc.); molecules that inhibit base excision repair (e.g., methoxyamine, NCS-666715, NSC-124854, etc.); molecules that inhibit mismatch repair (e.g., temozolomide in combination with NCS-666715 or NSC-124854, etc.); molecules that inhibit nucleotide excision repair (e.g., trabectedin. ET-743, etc.); molecules that inhibit double stranded break repair (e.g., RI-1, etc.); molecules that inhibit nonhomologous end joining (e.g., CC-115, CC-122, A12B4C3, etc.) (see, Kelley et al., "Targeting DNA repair pathways for cancer treatment: what's new?" *Future Oncol*. (2014) 10(7): pp 1215-1237.) Kelley et al. provides additional examples of molecules that inhibit the aforementioned types of DNA repair.

In other embodiments, gene expression profiling and analysis may be utilized to identify tumor cell lines likely to respond to treatment with the crystalline DBD polymorph or compositions thereof or in combination with other therapies including chemical, radiation, and other chemotherapeutics.

In preferred embodiments, the crystalline polymorph described herein has synergism with other anticancer therapies. Examples of preferred anti-cancer therapies that can be administered in combination with the crystalline polymorph as described herein, include, cyclophosphamide, 5-fluorouracil, adriamycin and BCNU.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
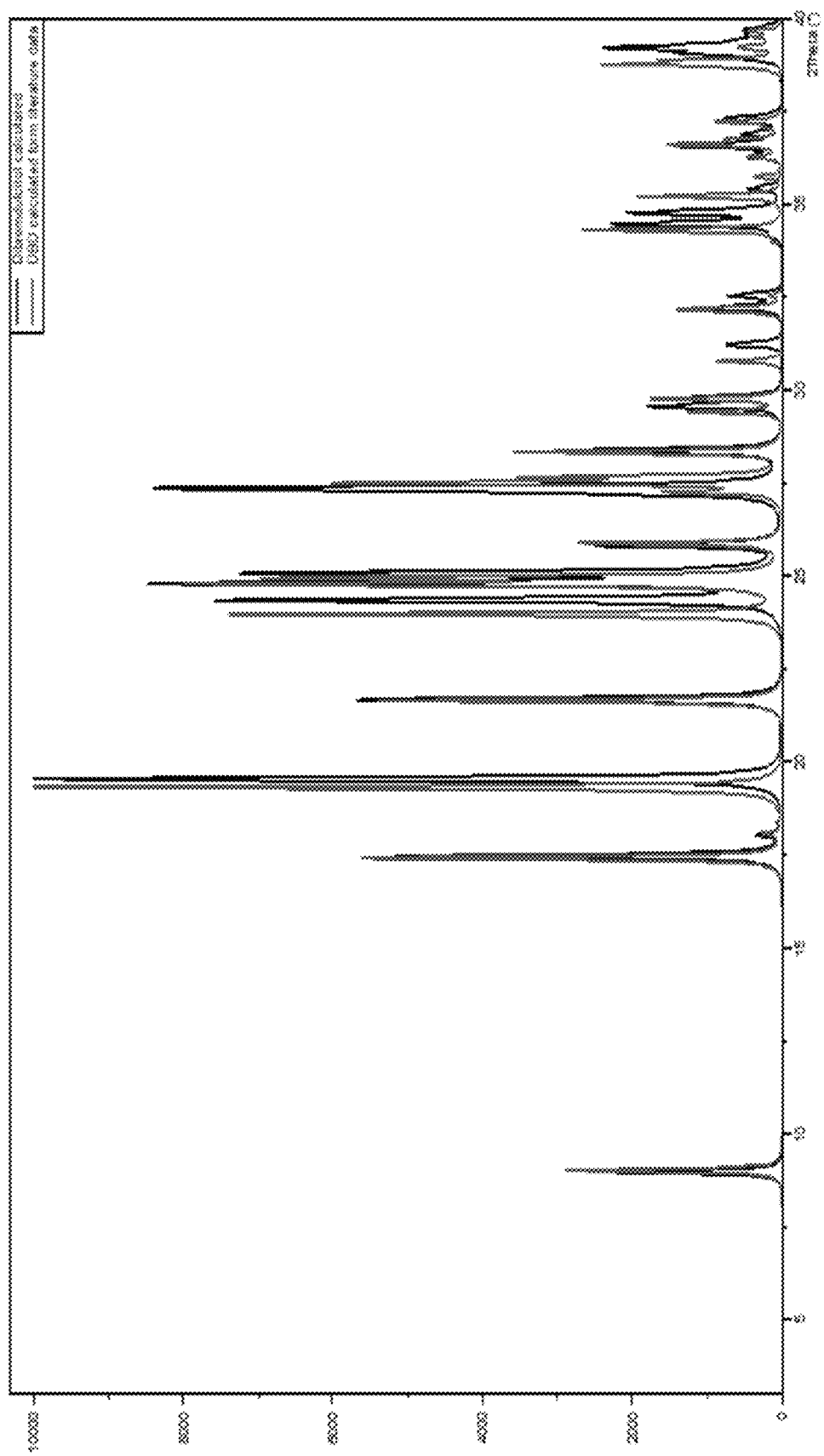
FIG. 1 represents an illustrative X-ray Powder Diffraction Pattern of the new crystalline DBD polymorph (black line) as compared to the calculated pattern for DBD (red line) as reported in *Acta. Cryst*. (1971) B27, 806-815.

While certain embodiments of the present invention have been shown and described herein, it will be obvious to those skilled in the art that such embodiments are provided by way of example only. Numerous variations, changes, and substitutions will occur to those skilled in the art without departing from the invention. It should be understood that various alternatives to the embodiments described herein are, in some circumstances, employed in practicing the invention. It is intended that the following claims define the scope of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

Definitions

Unless defined otherwise, all technical and scientific terms used herein have the same meaning as commonly understood by those of ordinary skill in the art, such as in the arts of peptide chemistry, cell culture, chemistry and biochemistry. Standard techniques are used for molecular biology, genetic and biochemical methods (see Sambrook et al., Molecular Cloning: A Laboratory Manual, 3rd ed., 2001, Cold Spring Harbor Laboratory Press, Cold Spring Harbor, N.Y.: Ausubel et al., Short Protocols in Molecular Biology (1999) 4th ed., John Wiley & Sons. Inc.), which are incorporated herein by reference.

The term "subject", as used herein in reference to individuals suffering from a disorder and encompasses mammals and non-mammals. In one embodiment of the methods and compositions provided herein, the mammal is a human.

The terms "effective amount", "therapeutically effective amount" or "pharmaceutically effective amount" as used herein, refer to an amount of at least one agent or compound being administered that is sufficient to treat the particular disease or condition. The result is the reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case is determined using techniques such as a dose escalation study. Additionally, "effective amount". "therapeutically effective amount" or "pharmaceutically effective amount" means that compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

The term "substantially the same as" as used herein, refers to a powder x-ray diffraction pattern or differential scanning calorimetry pattern that is non-identical to those depicted herein, but that falls within the limits of experimental error, when considered by one of ordinary skill in the art.

Figure 2:
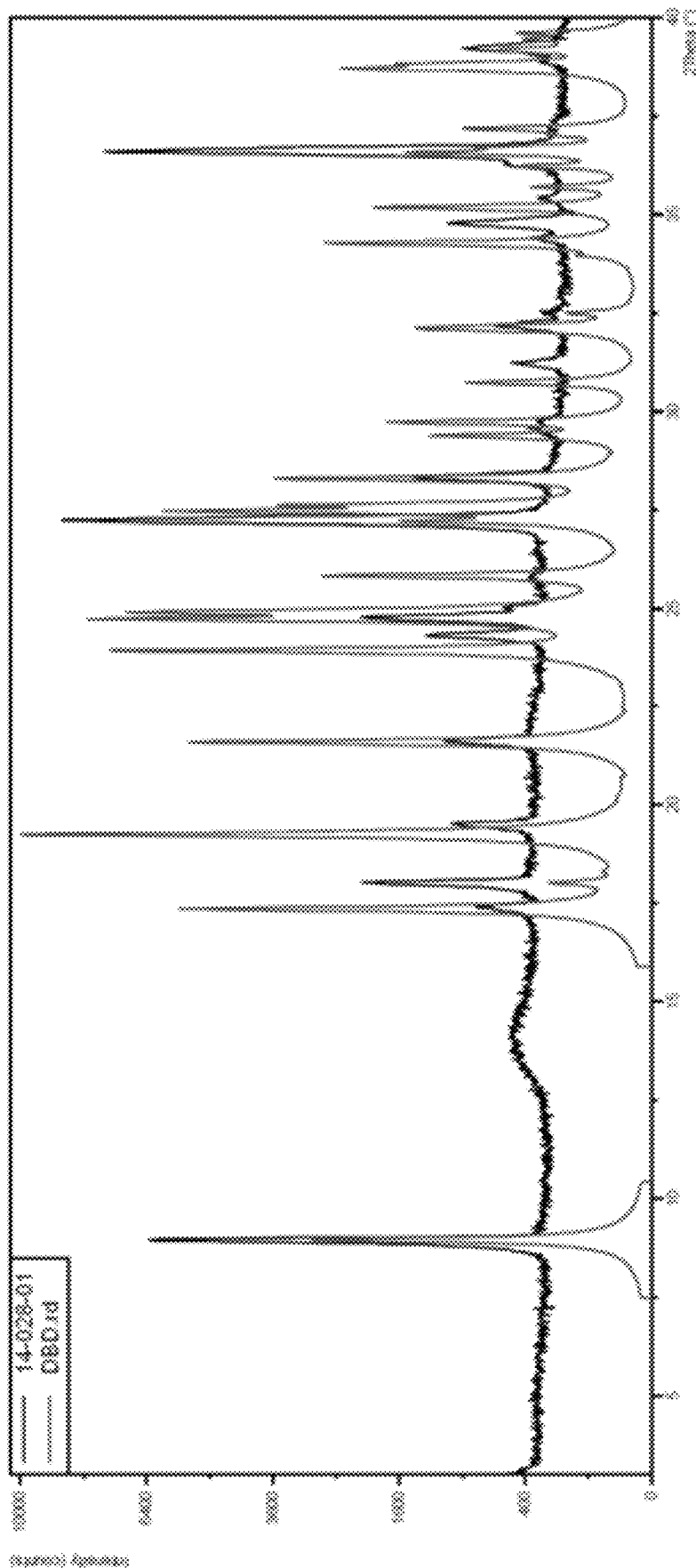
FIG. 2 represents an illustrative X-ray Powder Diffraction Pattern of another sample of the new crystalline DBD polymorph (black line) as compared to the calculated pattern for DBD (red line) as reported in *Acta. Cryst*. (1971) B27, 806-815.
Figure 3:
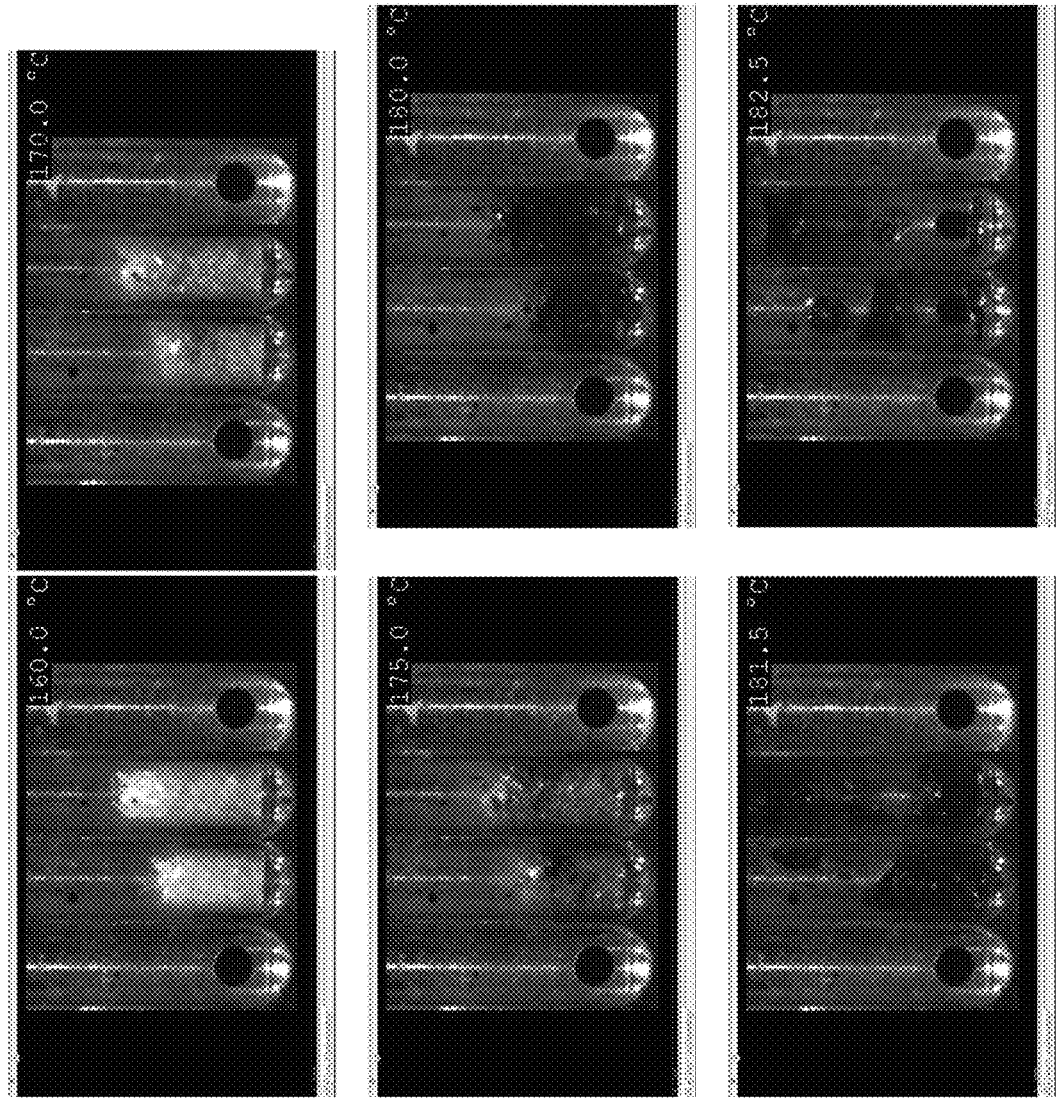
FIG. 3 represents Differential Scanning Calorimetry pattern of the crystalline DBD polymorph.
Figure 4:
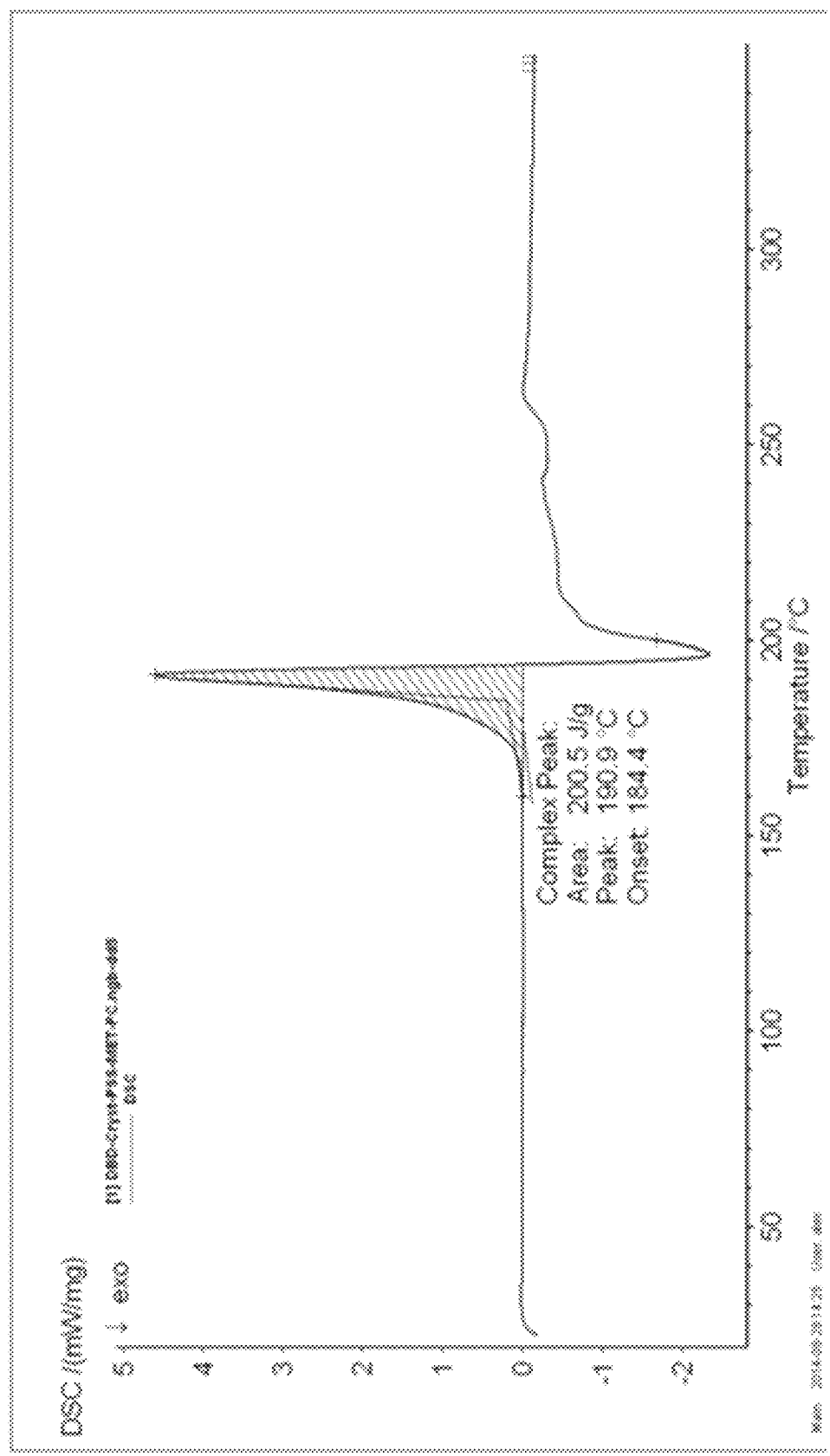
FIG. 4 represents Differential Scanning Calorimetry pattern of the crystalline DBD polymorph, showing endothermic onset at 184.4° C. and peak at approximately 191° C.

The terms "crystalline DBD polymorph" or "crystalline polymorph" or "crystalline polymorphic form of DBD" refers to a crystalline form of 1,6-Dibromo-1,6-dideoxy-dulcitol that exhibits an x-ray powder diffraction pattern substantially the same as that shown in FIG. 1, and/or FIG. 2 and/or as described in Tables 1-3, and/or a differential scanning calorimetry profile substantially the same as that shown in FIG. 3 and/or FIG. 4, or shown in FIGS. 5-9. The crystalline DBD polymorph described herein does not include the crystal structure of DBD as reported previously in *Acta. Cryst.* (1971) B27, 806-815.

As used herein, "DBD" refers to 1,6-dibromo-1,6-dideoxy-dulcitol having the crystal structure as reported in the literature in *Acta. Cryst.* (1971) B27, 806-815.

In the present invention, a "tumor" is defined as a population of heterogeneous cells, collectively forming a mass of tissue in a subject resulting from the abnormal proliferation of malignant cancer cells. Thus, a "tumor" will contain both normal or "non-cancerous" cells and "cancer" or "cancerous" cells.

Other aspects and embodiments of the invention provide the aspects and embodiments described above with the term "comprising" replaced by the term "consisting of" and the aspects and embodiments described above with the term "comprising" replaced by the term "consisting essentially of".

As used herein, "and/or" is to be taken as specific disclosure of each of the two specified features or components with or without the other. For example "A and/or B" is to be taken as specific disclosure of each (i) A, (ii) B and (iii) A and B, just as if each is set out individually.

As used herein, the term "about" is used to refer to an amount that is approximately, nearly, almost, or in the vicinity of being equal to or is equal to a stated amount, e.g., the state amount plus/minus about 5%, about 4%, about 3%, about 2% or about 1%. As it relates to XRPD, "about" is defined to include experimental error, such as 0.1-0.2 2θ, as has been reported in Ivanisevic et al, and Bhattacharya et al., both of which citing U.S. Pharmacopeia 2009.

It is to be understood that the application discloses all combinations of any of the above aspects and embodiments described above with each other, unless the context demands otherwise. Similarly, the application discloses all combinations of the preferred and/or optional features either singly or together with any of the other aspects, unless the context demands otherwise.

Polymorphic Forms of
1,6-Dibromo-1,6-Dideoxy-Dulcitol

The present invention relates to polymorphic forms of 1,6-dibromo-1,6-dideoxy-dulcitol (dibromo dulcitol or DBD), which is a known antitumor agent.

The present invention also relates to solid pharmaceutical compositions, comprising, as an active ingredient, an effective amount of the crystalline DBD polymorph. Also described are processes for the preparation of the crystalline DBD polymorph.

The present invention also relates to methods for treating a tumor, including cancer, comprising administering an effective amount of the crystalline DBD polymorph. Preferred tumors/cancer that can be treated using the crystalline DBD polymorph includes, but is not limited to, an adenocarcinoma, sarcoma, skin cancer, melanoma, bladder cancer, brain cancer, breast cancer, uterine cancer, ovarian cancer, prostate cancer, lung cancer, colorectal cancer, cervical cancer, liver cancer, head and neck cancer, esophageal cancer, pancreas cancer, pancreatic ductal adenocarcinoma (PDA), renal cancer, stomach cancer, multiple myeloma or cerebral cancer. In even further embodiments, the crystalline polymorph described herein can be used to treat brain, head and neck, lymphoma, melanoma, breast, cervical, and other cancers of the central nervous system. In even further preferred embodiments, the crystalline polymorph described herein can be used to treat pediatric cancers, such as pediatric brain cancer and pediatric leukemia. Other preferred cancers that can be treated with the crystalline polymorph described herein include, pulmonary (e.g., non-small cell lung cancer), gastric, renal, ovarian, uterine, colonic and bladder carcinomas, as well as in brain tumors and sarcomas.

The present invention also relates to methods for treating metastatic cancers comprising administering an effective amount of the crystalline DBD polymorph or compositions thereof. Preferred cancers that can be treated include cancers that have metastasized to the brain, including but not limited to, cancers originating from breast cancer, lung cancer, colon cancer, kidney cancer, pancreatic cancer, or malignant melanomas.

In preferred embodiments, the crystalline polymorph described herein has synergism with other anticancer therapies. Examples of preferred anti-cancer therapies that act synergistically with the crystalline DBD polymorph, include but are not limited to, cyclophosphamide, 5-fluorouracil, adriamycin and BCNU.

The crystalline DBD polymorph exhibits an x-ray powder diffraction pattern substantially the same as the x-ray powder diffraction pattern shown in FIG. 1 and/or FIG. 2. In yet further embodiments, the crystalline polymorph exhibits an x-ray powder diffraction pattern substantially the same as the x-ray powder diffraction pattern described in Table 1.

TABLE 1

| Pos. [°2 Th.] | Height [cts] | FWHM [°2Th.] | d-spacing [Å] | Rel. Int. [%] |
| --- | --- | --- | --- | --- |
| 9.0070 | 2007.16 | 0.0984 | 11.40028 | 20.18 |
| 17.4991 | 4997.70 | 0.0787 | 5.88470 | 50.25 |
| 18.0695 | 291.73 | 0.0984 | 5.70039 | 2.93 |
| 19.5783 | 9944.99 | 0.0787 | 5.26489 | 100.00 |
| 21.7114 | 5709.48 | 0.0984 | 4.75296 | 57.41 |
| 24.3807 | 7907.78 | 0.0787 | 4.23922 | 79.52 |
| 24.8403 | 8852.99 | 0.0787 | 4.16199 | 89.02 |
| 25.1116 | 7076.79 | 0.0984 | 4.11772 | 71.16 |
| 25.8683 | 2549.22 | 0.0984 | 3.99923 | 25.63 |
| 27.4122 | 7630.65 | 0.1378 | 3.77795 | 76.73 |
| 28.3897 | 3476.90 | 0.0984 | 3.65040 | 34.96 |
| 29.5985 | 1938.92 | 0.0787 | 3.50446 | 19.50 |
| 29.8176 | 1515.81 | 0.0787 | 3.47928 | 15.24 |
| 31.2628 | 827.09 | 0.0787 | 3.32218 | 8.32 |
| 32.2385 | 1039.22 | 0.0787 | 3.22418 | 10.45 |
| 32.5748 | 783.27 | 0.0787 | 3.19178 | 7.88 |
| 34.1817 | 140.60 | 0.0787 | 3.04590 | 1.41 |
| 34.4987 | 2541.50 | 0.0787 | 3.01876 | 25.56 |
| 34.8140 | 2270.52 | 0.0787 | 2.99225 | 22.83 |
| 35.4543 | 470.76 | 0.0984 | 2.93990 | 4.73 |
| 36.3168 | 479.65 | 0.0787 | 2.87235 | 4.82 |
| 36.6117 | 1587.89 | 0.0984 | 2.85000 | 15.97 |
| 36.9206 | 547.66 | 0.0787 | 2.82697 | 5.51 |
| 37.2904 | 952.98 | 0.0787 | 2.79992 | 9.58 |
| 38.9343 | 543.89 | 0.0590 | 2.68600 | 5.47 |
| 39.1132 | 1528.60 | 0.0720 | 2.67226 | 15.37 |
| 39.2640 | 2350.36 | 0.0787 | 2.66433 | 23.63 |
| 39.4717 | 569.04 | 0.0720 | 2.64894 | 5.72 |
| 39.6271 | 427.69 | 0.0590 | 2.64088 | 4.30 |
| 39.7626 | 395.82 | 0.0787 | 2.63224 | 3.98 |

In one aspect described herein are crystalline polymorphic forms of 1,6-dibromo-1,6-dideoxy-dulcitol characterized by peaks at 19.59° (100,00) and 24.380° (79,52) and 31.260° (8,32) and 34.500° (25,56) and 34.810° (22,83) and 39.260° (23,63) at 2θ±0.1°. In further embodiments, such a crystalline polymorph is further characterized by at least two peaks selected from 19.59° (100,00) and 24.380° (79,52) and 31.260° (8,32) and 34.500° (25,56) and 34.810° (22,83) and 39.260° (23,63) at 2θ±0.10. In further embodiments, such a crystalline polymorph is further characterized by at least three peaks selected from 19.59° (100,00) and 24.380° (79,52) and 31.260° (8,32) and 34.500° (25,56) and 34.810° (22,83) and 39.260 (23,63) at 2θ±0.10. In further embodiments, such a crystalline polymorph is further characterized by at least four peaks selected from 19.59° (100,00) and 24.380° (79,52) and 31.260° (8,32) and 34.500° (25,56) and 34.810° (22,83) and 39.260° (23,63) at 2θ±0.1°. In further embodiments, such a crystalline polymorph is further characterized by at least five peaks selected from 19.59° (100,00) and 24.380° (79,52) and 31.260° (8,32) and 34.500° (25,56) and 34.810° (22,83) and 39.260° (23,63) at 2θ±0.1°.

In yet further embodiments the crystalline DBD polymorph exhibits the Unit Cell Dimensions as described in Table 2. Preferably, the crystalline DBD polymorph comprises a beta angle of 96° as compared to the reported beta angle of 98° in *Acta. Cryst.* (1971) B27, 806-815.

TABLE 2

| Unit Cell Dimensions | Crystalline Polymorphic Form 1 | Literature |
| --- | --- | --- |
| a | 4.8489(8) Å | 4.874 ± 0.004 Å |
| b | 5.2414(10) Å | 5.269 ± 0.006 Å |
| C | 19.744(3) Å | 19.812 ± 0.007 Å |
| α | 90° | 90° |
| β | 96.438(13)° | 98.05 ± 0.1° |
| γ | 90° | 90° |

In certain instances, the crystalline DBD polymorph exhibits increased stability as compared to the literature reported form. In some instances, the improved stability of the crystalline DBD polymorph provides for the preparation of pharmaceutical dosage forms displaying reduced variability in the dosage present in a given dosage form, reduction in the presence of impurities in the final pharmaceutical product, and an improved shelf life of formulated dosage forms as compared to the pharmaceutical dosage form prepared with literature reported form. In some embodiments, a polymorph described herein demonstrates no degradation (e.g., less than 0.01%, less than 0.1%, less than 0.5% by wt.) for at least 3 months under accelerated conditions (e.g., 40° C.-75% RH), for at least 4 months under accelerated conditions (e.g., 40° C.-75% RH), for at least 5 months under accelerated conditions (e.g., 40° C.-75% RH), for at least 6 months under accelerated conditions (e.g., 40° C.-75% RH), for at least 9 months under accelerated conditions (e.g., 40° C.-75% RH), for at least 12 months under accelerated conditions (e.g., 40° C.-75% RH), and/or (ii) for at least 12 months under long-term conditions (e.g., 25° C.-60% RH), for at least 18 months under long-term conditions (e.g., 25° C.-60% RH), or for at least 24 months under long-term conditions (e.g., 25° C.-60% RH).

Pharmaceutical Compositions

The present invention also relates to pharmaceutical compositions comprising an effective amount of the crystalline polymorphic form of DBD. In some embodiments, the pharmaceutical compositions comprise an effective amount of a polymorphic form of DBD, as described herein, and at least one pharmaceutically acceptable carrier. In some embodiments, the pharmaceutical compositions comprise an effective amount of the crystalline DBD polymorph, as described herein, and at least one pharmaceutically acceptable carrier. In some embodiments the pharmaceutical compositions are for the treatment of disorders. In some embodiments the pharmaceutical compositions are for the treatment of disorders in a mammal. In some embodiments the pharmaceutical compositions are for the treatment of disorders in a human. In some embodiments the pharmaceutical compositions are for the treatment of cancers and/or hyperproliferative disorders.

More specifically and in preferred embodiments, a pharmaceutical composition may comprise, in addition to the crystalline polymorph described herein, one or more pharmaceutically acceptable carriers, adjuvants, excipients, diluents, fillers, buffers, stabilizers, preservatives, lubricants, or other materials well known to those skilled in the art. Suitable materials will be sterile and pyrogen-free, with a suitable isotonicity and stability. Examples include sterile saline (e.g. 0.9% NaCl), water, dextrose, glycerol, ethanol or the like or combinations thereof. Such materials should be non-toxic and should not interfere with the efficacy of the active compound. The precise nature of the carrier or other material will depend on the route of administration, which may be by bolus, infusion, injection or any other suitable route, as discussed below. Suitable materials will be sterile and pyrogen free, with a suitable isotonicity and stability. Examples include sterile saline (e.g. 0.9% NaCl), water, dextrose, glycerol, ethanol or the like or combinations thereof. The composition may further contain auxiliary substances such as wetting agents, emulsifying agents, pH buffering agents or the like.

Suitable carriers, excipients, etc. can be found in standard pharmaceutical texts, for example, Remington's Pharmaceutical Sciences, 18th edition, Mack Publishing Company. Easton, Pa., 1990.

In some preferred embodiments, the crystalline polymorph described herein is provided in a lyophilized form for reconstitution prior to administration. For example, lyophilized reagents may be re-constituted in sterile water and mixed with saline prior to administration to a subject.

The formulations may conveniently be presented in unit dosage form and may be prepared by any methods well known in the art of pharmacy. Such methods include the step of bringing into association the active compound with the carrier which constitutes one or more accessory ingredients. In general, the formulations are prepared by uniformly and intimately bringing into association the active compound with liquid carriers or finely divided solid carriers or both, and then if necessary shaping the product.

Additional formulations may be in the form of liquids, solutions, suspensions, emulsions, elixirs, syrups, tablets, lozenges, granules, powders, capsules, cachets, pills, ampoules, suppositories, pessaries, ointments, gels, pastes, creams, sprays, mists, foams, lotions, oils, boluses, electuaries, or aerosols. Optionally, other therapeutic or prophylactic agents may be included in a pharmaceutical composition or formulation.

Treatment may be any treatment and therapy, whether of a human or an animal (e.g. in veterinary applications), in which some desired therapeutic effect is achieved, for example, the inhibition or delay of the progress of the condition, and includes a reduction in the rate of progress, a halt in the rate of progress, amelioration of the condition, cure or remission (whether partial or total) of the condition, preventing, delaying, abating or arresting one or more symptoms and/or signs of the condition or prolonging survival of a subject or patient beyond that expected in the absence of treatment.

Treatment as a prophylactic measure (i.e. prophylaxis) is also included. For example, a subject susceptible to or at risk of the occurrence or re-occurrence of cancer may be treated as described herein. Such treatment may prevent or delay the occurrence or re-occurrence of cancer in the subject.

In particular, treatment may include inhibiting cancer growth, including complete cancer remission, and/or inhibiting cancer metastasis. Cancer growth generally refers to any one of a number of indices that indicate change within the cancer to a more developed form. Thus, indices for measuring an inhibition of cancer growth include a decrease in cancer cell survival, a decrease in tumor volume or morphology (for example, as determined using computed tomographic (CT), sonography, or other imaging method), a delayed tumor growth, a destruction of tumor vasculature, improved performance in delayed hypersensitivity skin test, an increase in the activity of cytolytic T-lymphocytes, and a decrease in levels of tumor-specific antigens. Reducing immune suppression in cancerous tumors in a subject may improve the capacity of the subject to resist cancer growth, in particular growth of a cancer already present the subject and/or decrease the propensity for cancer growth in the subject.

It will be appreciated that appropriate dosages of the crystalline DBD polymorph can vary from patient to patient. Determining the optimal dosage will generally involve the balancing of the level of therapeutic benefit against any risk or deleterious side effects of the administration. The selected dosage level will depend on a variety of factors including, but not limited to, the route of administration, the time of administration, the rate of excretion of the active compound, other drugs, compounds, and/or materials used in combination, and the age, sex, weight, condition, general health, and prior medical history of the patient. The amount of active compounds and route of administration will ultimately be at the discretion of the physician, although generally the dosage will be to achieve concentrations of the active compound at a site of therapy without causing substantial harmful or deleterious side-effects.

In general, a suitable dose of the crystalline DBD polymorph is in the range of about 100 μg to about 250 mg per kilogram body weight of the subject per day. Where the crystalline DBD polymorph is a salt, an ester, prodrug, or the like, the amount administered is calculated on the basis of the parent compound and so the actual weight to be used is increased proportionately.

Administration in vivo can be effected in one dose, continuously or intermittently (e.g., in divided doses at appropriate intervals). Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the physician.

The crystalline DBD polymorph or pharmaceutical compositions comprising the crystalline DBD polymorph may be administered to a subject by any convenient route of administration, whether systemically/peripherally or at the site of desired action, including but not limited to, oral (e.g. by ingestion); and parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrasternal; by implant of a depot, for example, subcutaneously or intramuscularly. Usually administration will be by the intravenous route, although other routes such as intraperitoneal, subcutaneous, transdermal, oral, nasal, intramuscular or other convenient routes are not excluded.

The pharmaceutical compositions comprising the crystalline DBD polymorph may be formulated in suitable dosage unit formulations appropriate for the intended route of administration.

Formulations suitable for oral administration (e.g. by ingestion) may be presented as discrete units such as capsules, cachets or tablets, each containing a predetermined amount of the crystalline DBD polymorph; as a powder or granules; as a solution or suspension in an aqueous or non-aqueous liquid; or as an oil-in-water liquid emulsion or a water-in-oil liquid emulsion; as a bolus; as an electuary; or as a paste.

A tablet may be made by conventional means. e.g., compression or molding, optionally with one or more accessory ingredients. Compressed tablets may be prepared by compressing in a suitable machine the active compound in a free-flowing form such as a powder or granules, optionally mixed with one or more binders (e.g. povidone, gelatin, acacia, sorbitol, tragacanth, hydroxypropylmethyl cellulose); fillers or diluents (e.g. lactose, microcrystalline cellulose, calcium hydrogen phosphate): lubricants (e.g. magnesium stearate, talc, silica); disintegrants (e.g. sodium starch glycolate, cross-linked povidone, cross-linked sodium carboxymethyl cellulose): surface-active or dispersing or wetting agents (e.g. sodium lauryl sulfate); and preservatives (e.g. methyl p hydroxybenzoate, propyl p-hydroxybenzoate, sorbic acid). Molded tablets may be made by molding in a suitable machine a mixture of the powdered compound moistened with an inert liquid diluent. The tablets may optionally be coated or scored and may be formulated so as to provide slow or controlled release of the crystalline DBD polymorph therein using, for example, hydroxypropylmethyl cellulose in varying proportions to provide the desired release profile. Tablets may optionally be provided with an enteric coating, to provide release in parts of the gut other than the stomach.

Formulations suitable for parenteral administration (e.g. by injection, including cutaneous, subcutaneous, intramuscular, intravenous and intradermal), include aqueous and non-aqueous isotonic, pyrogen-free, sterile injection solutions which may contain anti-oxidants, buffers, preservatives, stabilizers, bacteriostats, and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. Examples of suitable isotonic vehicles for use in such formulations include Sodium Chloride Injection, Ringer's Solution, or Lactated Ringer's Injection. Typically, the concentration of the active compound in the solution is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets. Formulations may be in the form of liposomes or other microparticulate systems which are designed to target the active compound to blood components or one or more organs.

Compositions comprising crystalline polymorph form described herein may be prepared in the form of a concentrate for subsequent dilution, or may be in the form of divided doses ready for administration. Alternatively, the reagents may be provided separately within a kit, for mixing prior to administration to a human or animal subject.

Modes of Administration, Formulations and Dosage Forms

Pharmaceutical compositions comprising the crystalline DBD polymorph are described herein. The compound, compound forms and compositions described herein are administered either alone, or in combination with, pharmaceutically acceptable carriers, excipients, or diluents in a pharmaceutical composition, according to standard pharmaceutical practice. Administration is effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route depends upon, for example, the condition and disorder of the recipient. Those of skill in the art will be familiar with administration techniques that can be employed with the compounds, compound forms, compositions and methods described herein. By way of example only, the compounds, compound forms and compositions described herein are, in some embodiments, administered locally to the area in need of treatment, by for example, local infusion during surgery, topical application such as creams or ointments, injection, catheter, or implant, said implant made for example, out of a porous, non-porous, or gelatinous material, including membranes, such as sialastic membranes, or fibers. The administration is, in some embodiments, by direct injection at the site of a diseased tissue or organ.

The pharmaceutical compositions described herein are, for example, in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition is, in some embodiments, in unit dosage forms suitable for single administration of precise dosages. Pharmaceutical compositions include a compound or compound form as described herein as an active ingredient, and a conventional pharmaceutical carrier or excipient. In some embodiments these compositions include other or additional medicinal or pharmaceutical agents, carriers, adjuvants, etc.

In preferred embodiments, compositions comprising the crystalline DBD polymorph described herein may be formulated with polyethylene glycol (PEG), in a process referred to as PEGylation, thereby generating a PEGylated DBD polymorph for administration to a patient. A versatile technology based on repeating units of polyethylene glycol (PEG), PEGylation can involve both covalent and non-covalent attachment of PEG polymers to the crystalline DBD polymorph. PEG is a water-soluble, amphiphilic, nontoxic, and non-immunogenic compound that is safely cleared from the human body. At least seven approved macromolecular drugs administered parenterally utilize PEGylated compositions. Examples of PEGylated compositions include Oncaspar®, Adagen®, Pegasys®, PEG-Intron®, Neulasta®, Somavert®, and Macugen®.

PEGylation may improve the physicochemical properties of both large and small molecules. In preferred embodiments, the crystalline polymorph of DBD can undergo PEGylation, thereby altering absorption characteristics (e.g., having improved water solubility) as well as an altered therapeutic index (a measure of dosage to toxicity) of the crystalline polymorph of DBD. In some embodiments, PEGylation can increase the retention time of the DBD polymorph in the human body, thereby protecting such compositions from degradation and clearance by the renal system.

By "formulated with polyethylene glycol" it is meant that the crystalline DBD polymorph has one or more covalent and/or non-covalent attachments to one or more PEG polymers. For example, in some embodiments, PEGylated molecules may be generated by conjugating a PEG molecule to an amino group, to a thiol group, or to a carboxylate group of a protein or small molecule (see, Veronese et al., "PEGylation, successful approach to drug delivery" Drug Discovery Today Vol. 10 (2005) pp 1451).

In other embodiments, techniques to provide a more consistent (in terms of size) PEGlyated DBD polymorph may be employed. By using a discrete PEG with a specific molecular weight (as opposed to traditional techniques that produce and/or utilize a range of PEG polymers of different sizes), a more consistent (with regard to size and structure) PEGylated DBD polymorph can be generated. For example, Quanta Biodesign's dPEG product offers linear chains of 4-48 PEG subunits and branched structures of three to nine linear chains. As another example, PolyPEG technology from Polytherics Ltd. uses a poly(methacrylate) backbone to which a series of PEGs may be attached, allowing fine tuning of a resulting conjugate's properties (see, http://www.bioprocessintl.com/upstream-processing/biochemicals-raw-materials/pegylation-of-biologics-340623/).

Sites for PEGylation can be present or engineered into a small molecule, such as the crystalline DBD polymorph. In some embodiments, nucleophilic or other suitable sites may be engineered into a small molecule for PEGylation, in such a manner that activity of the compound is not altered. (see, http://www.pharmtech.com/benefits-and-challenges-pegylating-small-molecules?id=&sk=&date=&%0A%09%09%09&pageID=1).

In other embodiments, compositions comprising the PEGylated DBD polymorph described herein may be administered in combination with molecules that inhibit cellular DNA damage repair mechanisms and machinery. For example, in some embodiments, the cytotoxic properties of the PEGylated DBD polymorph may be enhanced by co-administration with polyADP-ribose polymerase protein (PARP) inhibitors, alkylating agents, or other molecules that inhibit DNA repair. For example, the PEGylated DBD polymorph may be administered in combination with PARP inhibitors including Olaparib, Talazoparib, MK-4827, BGB-290, 3-aminobenzamide, CEP 9722, Veliparib and Rucaparib. Accordingly, PARP inhibitors can be used to potentiate therapy of the PEGylated DBD polymorph, and thus, enhance its therapeutic benefit.

In still other embodiments, the PEGylated DBD polymorph can be administered in combination with alkylating agents. Specific examples of alkylating agents that inhibit DNA repair include: nitrogen mustards, such as mechlorethamine, cyclophosphamide, ifosfamide, melphalan, chlorambucil, and temozolomide; nitrosoureas, such as carmustine (BCNU), lomustine (CCNU), and semustine (methyl-CCNU); thylenimines/methylmelamine such as thriethylenemelamine (TEM), triethylene, thiophosphoramide (thiotepa), hexamethylmelamine (HMM, altretamine); alkyl sulfonates (including sulfonate esters) such as busulfan; triazines such as dacarbazine (DTIC); and metal salts such as carboplatin, cisplatin, and oxaliplatin.

In still other embodiments, the PEGylated DBD polymorph can be administered in combination with any molecule that blocks any of a variety of DNA repair pathways, including: molecules that block direct repair by inhibiting or depleting MGMT (e.g., temozolomide, $O^6$ benzylguanine, etc.); molecules that inhibit base excision repair (e.g., methoxyamine, NCS-666715, NSC-124854, etc.); molecules that inhibit mismatch repair (e.g., temozolomide in combination with NCS-666715 or NSC-124854, etc.): molecules that inhibit nucleotide excision repair (e.g., trabectedin, ET-743, etc.); molecules that inhibit double stranded break repair (e.g., RI-1, etc.); molecules that inhibit nonhomologous end joining (e.g., CC-115, CC-122, A12B4C3, etc.) (see. Kelley et al., "Targeting DNA repair pathways for cancer treatment: what's new?" *Future Oncol*. (2014) 10(7): pp 1215-1237.) Kelley et al. provides additional examples of molecules that inhibit the aforementioned types of DNA repair.

In preferred embodiments, the cancer that is treated using the PEGylated polymorph of DBD is an adenocarcinoma, sarcoma, skin cancer, melanoma, bladder cancer, brain cancer, breast cancer, uterine cancer, ovarian cancer, prostate cancer, lung cancer, colorectal cancer, cervical cancer, liver cancer, head and neck cancer, esophageal cancer, pancreas cancer, pancreatic ductal adenocarcinoma (PDA), renal cancer, stomach cancer, multiple myeloma or cerebral cancer. In even further embodiments, the PEGylated DBD polymorph described herein can be used to treat brain, head and neck, lymphoma, melanoma, breast, cervical, and other cancers of the central nervous system. In even further preferred embodiments, the PEGylated DBD polymorph described herein can be used to treat pediatric cancers, such as pediatric brain cancer and pediatric leukemia. Other preferred cancers that can be treated with the PEGylated DBD polymorph described herein include, pulmonary (e.g., non-small cell lung cancer), gastric, renal, ovarian, uterine, colonic and bladder carcinomas, as well as in brain tumors and sarcomas.

In other embodiments, the cancer that is treated using the PEGylated polymorph of DBD is a cancer that has metastasized to the brain, including but not limited to cancer originating from breast cancer, lung cancer, colon cancer, kidney cancer, pancreatic cancer, or malignant melanomas.

In other embodiments, the PEGylated DBD polymorph may be used in combination with other therapeutic treatments, such as radiation therapy. Radiation therapy may be administered using any radiation-delivering system, including gantry-based systems, robotic radiosurgery systems, subcutaneous implants, radioisotopes, etc.

Doses

The amount of pharmaceutical compositions administered will firstly be dependent on the mammal being treated. In the instances where pharmaceutical compositions are administered to a human subject, the daily dosage will normally be determined by the prescribing physician with the dosage generally varying according to the age, sex, diet, weight, general health and response of the individual patient, the severity of the patient's symptoms, the precise indication or condition being treated, the severity of the indication or condition being treated, time of administration, route of administration, the disposition of the composition, rate of excretion, drug combination, and the discretion of the prescribing physician. Also, the route of administration vary depending on the condition and its severity. The pharmaceutical composition is, in some embodiments, in unit dosage form. In such form, the preparation is subdivided into unit doses containing appropriate quantities of the active component, e.g., an effective amount to achieve the desired purpose. Determination of the proper dosage for a particular situation is within the skill of the art. For convenience, in some embodiments, the total daily dosage is divided and administered in portions during the day if desired. The amount and frequency of administration will be regulated according to the judgment of the attending clinician physician considering such factors as described above. Thus the amount of pharmaceutical composition to be administered is variable depending upon the circumstances. Administration occurs in an amount of between about 0.001 mg/kg of body weight to about 100 mg/kg of body weight per day (administered in single or divided doses), or at least about 0.1 mg/kg of body weight per day. A particular therapeutic dosage includes, in some embodiments, from about 0.01 mg to about 7000 mg of compound, or, from about 0.05 mg to about 2500 mg. The quantity of crystalline DBD polymorph in a unit dose of preparation is, in some embodiments, varied or adjusted from about 0.1 mg to 1000 mg, from about 1 mg to 300 mg, or 10 mg to 200 mg, according to the particular application. In some instances, the particular therapeutic dosage is about 200 mg, about 300 mg, about 400 mg, about 500 mg, about 600 mg, about 700 mg or about 800 mg. In some instances, dosage levels below the lower limit of the aforesaid range are more than adequate, while in other cases still larger doses are employed without causing any harmful side effect, e.g. by dividing such larger doses into several small doses for administration throughout the day. In combinational applications in which the compound is not the sole therapy, it is possible to administer lesser amounts of compound and still have therapeutic or prophylactic effect.

In preferred embodiments, the crystalline polymorphic form described herein is administered at about 2.5 to 3.5 mg/kg/day for 5-7 weeks per os. In further preferred embodiments, the crystalline polymorphic form described herein is administered at about 4-5 mg/kg/day for 10-20 days per os, repeated monthly.

Combination Therapies

The crystalline DBD polymorph described herein can be administered as a sole therapy or in combination with another therapy or therapies.

By way of example only, if one of the side effects experienced by a patient upon receiving a compound or compound form as described herein is hypertension, then it may be appropriate to administer an anti-hypertensive agent in combination with the crystalline DBD polymorph. Or, by way of example only, the therapeutic effectiveness of the crystalline DBD polymorph as described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering the crystalline DBD polymorph with another therapeutic agent (which also includes a therapeutic regimen) that also has therapeutic benefit. Regardless of the disease, disorder or condition being treated, the overall benefit experienced by the patient may simply be additive of the two therapeutic agents or the patient may experience a synergistic benefit.

In other preferred embodiments, the crystalline DBD polymorph or compositions thereof may be administered in combination with other therapeutic treatments, such as radiation-based therapy. The crystalline DBD polymorph (including compositions comprising the crystalline DBD polymorph, and where appropriate other chemotherapeutic agent(s)) may be administered concurrently (e.g., simultaneously, essentially simultaneously or within the same treatment protocol), sequentially or separately with the radiation therapy, depending upon the nature of the disease, the condition of the patient, and the actual choice of other therapies to be administered. By sequentially, it is meant that the radiation therapy may be administered prior to or subsequent to administration of the crystalline DBD polymorph or compositions thereof. By separately, it is meant that the crystalline DBD polymorph or compositions thereof and the radiation therapy are administered to the subject by two different routes of administration which occur at or about the same time.

Radiation therapy can be delivered in any preferred scheduling, i.e. concurrently or sequentially to administration of the crystalline DBD polymorph or compositions thereof. The radiation therapy can be delivered via any radiation-delivering system, apparatus, device, and/or molecule including but not limited to gantry-based devices, radiation delivering devices used during robotic radiosurgery, subcutaneous implants, and/or radioisotopes as indicated by a prescribed therapeutic schedule. Radiation therapy may be delivered by any available technique, including but not limited to 3D-conformal radiation therapy (3D-CRT) (e.g., delivered by linear accelerators), intensity modulated radiation therapy (IMRT), image-guided radiation therapy (IGRT), intraoperative radiation therapy (IORT), and so forth. Linear accelerators can deliver radiation to specifically targeted areas of the human body, including particular organs, regions, etc., while sparing surrounding healthy tissue. In other embodiments, radiation may be delivered internally, such as via brachytherapy, which can utilize radioactive seeds implanted near or at the site of the tumor. In still other embodiments, radiation can be delivered as an isotope into a vein.

In the instances where the crystalline DBD polymorph are administered with other therapeutic agents, they need not be administered in the same pharmaceutical composition as other therapeutic agents, and may, because of different physical and chemical characteristics, be administered by a different route. For example, the crystalline DBD polymorph may be administered orally to generate and maintain good blood levels thereof, while the other therapeutic agent may be administered intravenously. The determination of the mode of administration and the advisability of administration, where possible, in the same pharmaceutical composition, is well within the knowledge of the skilled clinician. The initial administration can be made according to established protocols known in the art, and then, based upon the observed effects, the dosage, modes of administration and times of administration can be modified by the skilled clinician.

The crystalline DBD polymorph (including compositions) (and where appropriate other chemotherapeutic agent) may be administered concurrently (e.g., simultaneously, essentially simultaneously or within the same treatment protocol) sequentially or separately, depending upon the nature of the disease, the condition of the patient, and the actual choice of other chemotherapeutic agent to be administered. For combinational applications and uses, the crystalline DBD polymorph and compositions described herein and the chemotherapeutic agent need not be administered simultaneously or essentially simultaneously. Thus, the crystalline DBD polymorph and compositions as described herein may be administered first followed by the administration of the chemotherapeutic agent; or the chemotherapeutic agent may be administered first followed by the administration of the crystalline DBD polymorph. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent may be administered first, especially if it is a cytotoxic agent, and then the treatment continued with the administration of the crystalline DBD polymorph followed, where determined advantageous, by the administration of the chemotherapeutic agent, and so on until the treatment protocol is complete. Thus, in accordance with experience and knowledge, the practicing physician can modify each administration protocol for treatment according to the individual patient's needs, as the treatment proceeds. The attending clinician, in judging whether treatment is effective at the dosage administered, will consider the general well-being of the patient as well as more definite signs such as relief of disease-related symptoms. Relief of disease-related symptoms such as pain, and improvement in overall condition can also be used to help judge effectiveness of treatment.

In preferred embodiments, administration in vivo can be effected in one dose, continuously or intermittently (e.g., in divided doses at appropriate intervals). Methods of determining the most effective means and dosage of administration are well known to those of skill in the art and will vary with the formulation used for therapy, the purpose of the therapy, the target cell being treated, and the subject being treated. Single or multiple administrations can be carried out with the dose level and pattern being selected by the physician.

In further preferred embodiments, administration of anti-cancer compounds and the crystalline polymorph form described herein may be simultaneous, separate or sequential. By "simultaneous" administration, it is meant that the anti-cancer compounds and the crystalline polymorph form described herein are administered to the subject in a single dose by the same route of administration.

By "separate" administration, it is meant that the anti-cancer compounds and the crystalline polymorph form described herein are administered to the subject by two different routes of administration which occur at or about the same time. This may occur for example where one agent is administered by infusion or parenterally and the other is given orally during the course of the infusion or parenteral administration.

By "sequential" it is meant that the anti-cancer compounds and the crystalline polymorph form described herein are administered at different points in time, provided that the activity of the first administered agent is present and ongoing in the subject at the time the second agent is administered. For example, the anti-cancer compounds may be administered first, followed by administration of the crystalline polymorph form described herein. Preferably, a sequential dose will occur such that the second of the two agents is administered within 48 hours, preferably within 24 hours, such as within 12, 6, 4, 2 or 1 hour(s) of the first agent.

In preferred embodiments, multiple doses of the crystalline polymorph form described herein may be administered, for example 2, 3, 4, 5 or more than 5 doses may be administered after administration of other the anti-cancer compounds. The administration of the crystalline polymorph form described herein may continue for sustained periods of time after administration of the anti-cancer compounds. For example, treatment with the crystalline polymorph form described herein may be continued for at least 1 week, at least 2 weeks, at least 3 weeks, at least 1 month or at least 2 months. Treatment with the crystalline polymorph form described herein may be continued for as long as is necessary to achieve complete tumor rejection.

In further preferred embodiments, multiple doses of the anti-cancer compounds may be administered, for example 2, 3, 4, 5 or more than 5 doses may be administered after administration of the crystalline polymorph form described herein. The administration of the anti-cancer compounds may continue for sustained periods of time after administration of the crystalline polymorph form described herein. For example, treatment with the anti-cancer compounds may be continued for at least 1 week, at least 2 weeks, at least 3 weeks, at least 1 month or at least 2 months. Treatment with the anti-cancer compounds may be continued for as long as is necessary to achieve complete tumor rejection.

In preferred embodiments, the crystalline polymorph described herein has synergism with other anticancer therapies. Examples of preferred anti-cancer therapies, include, cyclophosphamide, 5-fluorouracil, adriamycin and BCNU.

In other preferred embodiments, other chemotherapeutics that can be administered in combination with the crystalline polymorph of DBD described herein, include, but are not limited to: aspirin, sulindac, curcumin. alkylating agents (that may inhibit DNA repair) including: nitrogen mustards, such as mechlor-ethamine, cyclophosphamide, ifosfamide, melphalan, chlorambucil, and temozolomide; nitrosoureas, such as carmustine (BCNU), lomustine (CCNU), and semustine (methyl-CCNU); thylenimines/methylmelamine such as thriethylenemelamine (TEM), triethylene, thiophosphoramide (thiotepa), hexamethylmelamine (HMM, altretamine); alkyl sulfonates (including sulfonate esters) such as busulfan; triazines such as dacarbazine (DTIC); antimetabolites including folic acid analogs such as methotrexate and trimetrexate, pyrimidine analogs such as 5-fluorouracil, fluorodeoxyuridine, gemcitabine, cytosine arabinoside (AraC, cytarabine), 5-azacytidine, 2,2'-difluorodeoxycytidine, purine analogs such as 6-mercaptopurine, 6-thioguanine, azathioprine, 2'-deoxycoformycin (pentostatin), erythrohydroxynonyladenine (EHNA), fludarabine phosphate, and 2-chlorodeoxyadenosine (cladribine, 2-CdA); natural products including antimitotic drugs such as taxanes including paclitaxel, *vinca* alkaloids including vinblastine (VLB), vincristine, and vinorelbine, taxotere, estramustine, and estramustine phosphate; epipodophylotoxins such as etoposide and teniposide; antibiotics, such as actimomycin D, daunomycin (rubidomycin), doxorubicin, mitoxantrone, idarubicin, bleomycins, plicamycin (mithramycin), mitomycinC, and actinomycin; enzymes such as L-asparaginase, cytokines such as interferon (IFN)-gamma, tumor necrosis factor (TNF)-alpha, TNF-beta and GM-CSF, anti-angiogenic factors, such as angiostatin and endostatin, inhibitors of FGF or VEGF such as soluble forms of receptors for angiogenic factors, including soluble VGF/VEGF receptors, platinum or platinum coordination complexes (which may also act as alkylating agents) such as cisplatin, oxiliplatin and carboplatin, anthracenediones such as mitoxantrone, substituted urea such as hydroxyurea, methylhydrazine derivatives including N-methylhydrazine (MIH) and procarbazine, adrenocortical suppressants such as mitotane (o,p'-DDD) and aminoglutethimide; hormones and antagonists including adrenocorticosteroid antagonists such as prednisone and equivalents, dexamethasone and aminoglutethimide; progestin such as hydroxyprogesterone caproate, medroxyprogesterone acetate and megestrol acetate; estrogen such as diethylstilbestrol and ethinyl estradiol equivalents; antiestrogen such as tamoxifen; androgens including testosterone propionate and fluoxymesterone/equivalents; antiandrogens such as flutamide, gonadotropin-releasing hormone analogs and leuprolide; non-steroidal antiandrogens such as flutamide; kinase inhibitors, histone deacetylase inhibitors, methylation inhibitors, proteasome inhibitors, monoclonal antibodies, oxidants, anti-oxidants, telomerase inhibitors, BH3 mimetics, ubiquitin ligase inhibitors, stat inhibitors and receptor tyrosine kinase inhibitors such as imatinib mesylate (marketed as Gleevac or Glivac) and erlotinib (an EGF receptor inhibitor) now marketed as Tarveca; inhibitors of PI-3 kinase, including PI-3 kinasedelta; metabolic inhibitors, including Lonidamine and Levamisole; DNA repair inhibitors including poly ADP ribose polymerase (PARP) inhibitors such as Olaparib. BGB-290, MK-4827, 3-aminobenzamide, CEP 9722, Veliparib and Rucaparib; Iniparib; anti-angiogenics or angiogenesis inhibitors, including Axitinib, Bevacizumab, Cabozantinib, Everolimus, Lenalidomide, Pazopanib, Ramucirumab, Regorafenib, Sorafenib, Sunitinib, Thalidomide, Vandetanib, Ziv-aflibercept, and other monoclonal antibodies that inhibit angiogenesis; inhibitors of MGMT expression, including pseudosubstrate inhibitors of MGMT, such as $O^6$-benzylguanine, or RNA interference-nediated gene silencing of MGMT, or other inhibitors of MGMT such as Temozolomide. and Lomeguatrib; anti Her-2/neu drugs, including Trastuzumab, Ado-trastuzumab emtansine, Pertuzumab, and NeuVax™, and anti-virals such as oseltamivir phosphate, Amphotericin B, and palivizumab.

Diseases

Described herein are methods of treating a disease or disorder in an individual suffering from the disease or disorder comprising administering to said individual an effective amount of a polymorphic form of DBD as described herein. The invention extends to the use of the compounds, compound forms and compositions described herein, in the manufacture of a medicament for treating or preventing a disease or disorder.

In preferred embodiments, the cancer that is treated using the crystalline polymorph of DBD is an adenocarcinoma, sarcoma, carcinosarcoma, rhabdomyosarcoma, Crocker sarcoma, skin cancer, melanoma, bladder cancer, brain cancer, breast cancer, uterine cancer, ovarian cancer, prostate cancer, lung cancer, colorectal cancer, cervical cancer, liver cancer, head and neck cancer, esophageal cancer, pancreas cancer, pancreatic ductal adenocarcinoma (PDA), renal cancer, stomach cancer, multiple myeloma or cerebral cancer. In even further embodiments, the crystalline polymorph described herein can be used to treat brain, head and neck, lymphoma, melanoma, breast, cervical, and other cancers of the central nervous system. In even further preferred embodiments, the crystalline polymorph described herein can be used to treat pediatric cancers, such as pediatric brain cancer and pediatric leukemia. Other preferred cancers that can be treated with the crystalline polymorph described herein include, pulmonary (e.g., non-small cell lung cancer), gastric, renal, ovarian, uterine, colonic and bladder carcinomas, as well as in brain tumors and sarcomas.

In further preferred embodiments, the cancer that is treated using the crystalline polymorph of DBD includes, but not limited to, bladder cancer, breast cancer, colon cancer (colorectal), anal cancer, rectal cancer, esophageal cancer, including those with Barrett's esophagus, head and neck cancer, oral cavity/oropharyngeal cancer (e.g., oral squamous cell cancer), salivary cancer, endometrial cancer, cervical cancer, kidney (renal) cancer, lung cancer (including, but not limited to NSCLC, SCLC, squamous cell cancer), and melanoma.

In other embodiments, the cancer that is treated using the crystalline polymorph of DBD or compositions thereof is a cancer that has metastasized to the brain, including breast cancer, lung cancer, colon cancer, kidney cancer, pancreatic cancer or malignant melanomas.

As used herein, "brain cancer" means any of the following: astrocytoma, anaplastic astrocytoma, high grade astrocytoma, brainstem glioma, low grade gliomas, gliosarcoma, choroid plexus papilloma, ependymoma, glioblastomas, glioblastoma multiforme (GBM), medulloblastoma, refractory medulloblastoma, acoustic neuroma, lymphoma, meningioma, pineal gland tumor, pituitary adenoma, schwannoma, infiltrative astrocytoma, pilocytic astrocytoma, oligodendroglioma, mixed oligoastrocytoma, and/or ependymoma.

As used herein, "leukemia" means any of the following: acute lymphoblastic leukemia (ALL), acute myelogenous leukemia (AML), chronic lymphocytic leukemia (CLL), chronic myelogenous leukemia (CML), hairy cell leukemia, as well as subtypes of leukemia, such as, for example, acute promyelocytic leukemia (a subtype of AML).

As used herein. "cervical cancer" means any of the following: cervical carcinogenesis. Negative for Intraepithelial Lesion or Malignancy (NILM), Human Papilloma Virus (HPV) positive, Atypical Squamous Cells of Undetermined Significance (ASC-US), Low-grade Squamous Intraepithelial Lesion (LSIL), Atypical Squamous Cells. HSIL (ASC-H). Atypical Glandular Cells of Undetermined Significance (AGUS), High-grade Squamous Intraepithelial Lesion (HSIL), cervical dysplasia, pre-cancer, pre-malignant legion, cervical cancer, cervical adenocarcinoma, cervical squamous cell carcinoma, cervical intraepithelial neoplasia 1 (CIN1), cervical intraepithelial neoplasia (CIN2), cervical intraepithelial neoplasia 3 (CIN3), carcinoma in situ, invasive cervical carcinoma, and cytological or genetic abnormality of the cell.

As used herein, "oral cancer" means any of the following: oral carcinogenesis, pre-cancer, pre-malignant legion, oral cancer, oral adenocarcinoma, oral squamous cell carcinoma, oral carcinoma in situ, invasive oral carcinoma, leukoplakia, erythroplakia, oral lichen planus, oral submucous fibrosis, oral discoid lupus erythematosus, dyskeratosis congenital, epidermolysis bullosa, squamous cell carcinoma, verrucous carcinoma, minor salivary gland carcinoma, adenoid cystic carcinoma, mucoepidermoid carcinoma, polymorphous low-grade adenocarcinoma, oral lymphomas (including Hodgkin lymphoma and non-Hodgkin lymphoma), eosinophilic granuloma, fibroma, granular cell tumor, karatoacanthoma, leiomyoma, osteochondroma, lipoma, schwannoma, neurofibroma, papilloma, condyloma acuminatum, verrumciform xanthoma, pyogenic granuloma, rhabdomyoma, odontogenic tumors, nicotine stomatitis, tobacco pouch keratosis, proliferative verrucous leukoplakia, speckled leukoplakia, erythroleukoplakia, Actinic cheilosis, squamous cell carcinoma of the lip, basal cell carcinoma of the lip and cytological or genetic abnormality of the cell.

As used herein, "anal cancer" means any of the following: anal carcinogenesis, Human Papilloma Virus (HPV) positive, Atypical Squamous Cells of Undetermined Significance (ASC-US), Low-grade Squamous Intraepithelial Lesion (LSIL), Atypical Squamous Cells. HSIL (ASC-H), High-grade Squamous Intraepithelial Lesion (HSIL), Anal Squamous Intraepithelial Lesion (SIL), Low-grade anal dysplasia, High-grade anal dysplasia, Cloacogenic carcinoma, Anal basal cell carcinoma. Anal melanoma, pre-cancer, pre-malignant legion, anal cancer, anal adenocarcinoma, anal squamous cell carcinoma, anal intraepithelial neoplasia 1 (AIN1), anal intraepithelial neoplasia 1 (AIN2), anal intraepithelial neoplasia 1 (AIN3), carcinoma in situ, invasive anal carcinoma, and cytological or genetic abnormality of the cell.

As used herein, "bladder cancer" means any of the following: bladder carcinogenesis; atypical hyperplasia; papillary or nonpapillary carcinoma in situ (CIS); flat, papillary and atypical urothelial hyperplasia; urothelial papilloma; urothelial dysplasia; intestinal metaplasia; keratinising squamous metaplasia; verrucous squamous hyperplasia; condyloma *acuminatum*; Transitional cell (urothelial) carcinoma (TCC); Papillary carcinoma; Flat carcinoma; pre-cancer; pre-malignant legion; bladder cancer; bladder adenocarcinoma; bladder squamous cell carcinoma; bladder small-cell carcinoma; bladder sarcoma; and cytological or genetic abnormality of the cell.

As used herein. "breast cancer" means any of the following: breast carcinogenesis, breast carcinoma, pre-cancer, pre-malignant legion, breast cancer, carcinoma in situ, ductal carcinoma in situ (DCIS), ductal intraepithelial neoplasia (DIN), lobular intraepithelial neoplasia (LIN), atypical lobular hyperplasia, lobular carcinoma in situ, intraductal proliferative lesions with atypia, flat epithelial atypia (FEA), atypical ductal hyperplasia (ADH), Paget's disease of the nipple, sarcoma of the breast, medullary carcinoma, tubular carcinoma, mucinous carcinoma, metaplastic carcinoma, adenocystic carcinoma, phyllodes tumor, angiosarcoma, Invasive ductal carcinoma (IDC), Invasive lobular carcinoma (ILC), Endocrine-sensitive breast cancer, HER2-positive breast cancer, Triple-negative breast cancer (TNBC), Papillary carcinoma, Male breast cancer, micropapillary ductal carcinoma in situ, papillary ductal carcinoma in situ, solid ductal carcinoma in situ, cribriform ductal carcinoma in situ, comedo ductal carcinoma in situ, Inflammatory breast cancer (IBC), and cytological or genetic abnormality of the cell.

As used herein, "pulmonary cancer" and/or "lung cancer" means any of the following: pulmonary carcinogenesis, pulmonary dysplasia, pre-cancer, pre-malignant legion, lung cancer, squamous dysplasia (SD), carcinoma in situ (CIS), atypical adenomatous hyperplasia (AAH), diffuse idiopathic pulmonary neuroendocrine cell hyperplasia (DIP-NECH), basal cell hyperplasia, squamous metaplasia, adenomatous hyperplasia, angiogenic squamous dysplasia, pulmonary fibrosis, baseline metaplasia, low-grade dysplasia, high-grade dysplasia, human papillomavirus (HPV)-related respiratory papillomatosis, mesothelioma in situ, small cell lung cancer (SCLC), limited SCLC, extensive SCLC, non-small cell lung cancer (NSCLC), squamous cell lung cancer, pulmonary adenocarcinoma, large-cell undifferentiated carcinoma, occult stage NSCLC, and cytological or genetic abnormality of the cell.

As used herein, "melanoma" and/or "melanocyte cancer" means any of the following: melanocyte carcinogenesis, Actinic keratosis, Keratoacanthomas, Actinic cheilitis, Dysplastic nevi, Congenital melanocytic nevi. Lentigo maligna, cutaneous melanoma, ocular melanoma, mucosal melanoma, pre-cancer, pre-malignant legion, melanoma, and cytological or genetic abnormality of the cell.

As used herein, "esophageal cancer" means any of the following: esophageal carcinogenesis, esophageal dysplasia, pre-cancer, pre-malignant legion, esophageal cancer. Barrett's esophageal cancer, intestinal metaplasia, low-grade dysplasia, high-grade dysplasia, carcinoma in situ, esophageal adenocarcinoma, adenocarcinoma, esophageal squamous cell carcinoma, squamous cell carcinoma, and cytological or genetic abnormality of the cell.

As used herein, "renal cancer" or "kidney cancer" include any of the following types of cancer found in the kidneys: renal cell carcinoma (RCC) (also known as renal cell cancer or renal cell adenocarcinoma), clear cell renal cell carcinoma, papillary renal cell carcinoma, chromophobe renal cell carcinoma, collecting duct RCC, multilocular cystic RCC, medullary carcinoma, mucinous tubular and spindle cell carcinoma, Neuroblastoma-associated RCC, unclassified renal cell carcinoma, transitional cell carcinomas, Wilms tumors (nephroblastoma), and renal sarcomas.

As used herein, "endometrial cancer" include any of the following types of cancer found in the endometrium: endometrial carcinomas, adenocarcinomas, endometrioid adenocarcinoma, squamous cell, undifferentiated carcinoma, poorly differentiated carcinoma, clear-cell carcinoma, serous carcinoma (also called papillary serous carcinoma), poorly differentiated carcinoma, uterine carcinosarcoma (CS), uterine sarcomas, stromal sarcomas, and leiomyosarcomas.

As used herein, "colorectal cancer" and/or "colon cancer" include any of the following types of cancer found in the colon: colorectal adenocarcinoma, mucinous adenocarcinoma, signet ring cell adenocarcinoma, gastrointestinal carcinoid tumors, primary colorectal lymphomas, gastrointestinal stromal tumors, leiomyosarcomas, melanomas, and squamous cell carcinomas.

There are many types of salivary gland cancers as the normal salivary glands are made up of several different types of cells, and tumors can start in any of these cell types. Salivary gland cancers are named according to which of these cell types they most look like when seen under a microscope. As used herein. "salivary gland cancer" and/or "salivary cancer" include the following: mucoepidermoid carcinomas, adenoid cystic carcinoma, adenocarcinomas, acinic cell carcinoma, polymorphous low-grade adenocarcinoma (PLGA), adenocarcinoma, not otherwise specified (NOS), basal cell adenocarcinoma, clear cell carcinoma, cystadenocarcinoma, sebaceous adenocarcinoma, sebaceous lymphadenocarcinoma, mucinous adenocarcinoma, oncocytic carcinoma, salivary duct carcinoma, carcinoma ex pleomorphic adenoma, carcinosarcoma, and metastasizing mixed tumor, squamous cell carcinoma, epithelial-myoepithelial carcinoma, anaplastic small cell carcinoma, and undifferentiated carcinomas.

Besides salivary gland cancer, as used herein, "head and neck" cancer include laryngeal and hypopharyngeal cancer, nasal cavity and paranasal sinus cancer, nasopharyngeal cancer, oral and oropharyngeal cancer.

Kits

The compounds, compound forms, compositions and methods described herein provide kits for the treatment of diseases and disorders, such as the ones described herein.

These kits comprise a compound, compound form, compounds, compound forms or compositions described herein in a container and, optionally, instructions teaching the use of the kit according to the various methods and approaches described herein. Such kits, in some embodiments, also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein are provided, marketed and/or promoted to health providers, including physicians, nurses, pharmacists, formulary officials, and the like. Kits are also, in some embodiments, marketed directly to the consumer.

Provided in certain embodiments, are compositions or kits comprising a polymorph of DBD as described herein, a double low density polyethylene plastic bag, and an HDPE container. In further embodiments, the composition or kit further comprises a foil bag (e.g., an anhydrous foil bag, such as a heat sealed anhydrous foil bag). In some embodiments, the composition or kit further comprises a desiccant; in still other embodiments, a desiccant is not necessary and/or present. In some instances, such packing improves the stability of the crystalline polymorph of DBD as described herein.

Besides being useful for human treatment, the compounds, compound forms and pharmaceutical compositions described herein are also useful for veterinary treatment of animals. For example, in other preferred embodiments, the "patient" or "subject suitable for treatment" may be a mammal, such as a rodent (e.g. a guinea pig, a hamster, a rat, a mouse), murine (e.g. a mouse), canine (e.g. a dog), feline (e.g. a cat), equine (e.g. a horse), a primate, simian (e.g. a monkey or ape), a monkey (e.g. marmoset, baboon), an ape (e.g. gorilla, chimpanzee, orangutan, gibbon), or a human. In other embodiments, non-human mammals, especially mammals that are conventionally used as models for demonstrating therapeutic efficacy in humans (e.g. murine, primate, porcine, canine, or rabbit animals) may be employed.

The examples and preparations provided below further illustrate and exemplify the compounds of the present invention and methods of preparing such compounds. It is to be understood that the scope of the present invention is not limited in any way by the scope of the following examples and preparations.

EXAMPLES

Example 1: Preparation of Crystalline Polymorphic Form of DBD by Precipitation by a Supersaturated Solution The DBD sample as prepared by methods disclosed previously, was dissolved in mixture of methanol/water from 95:5 to 70:30 ratios and heated to boiling (approximately 65° C.) and then cooled. Preferably, the mixture comprises 70%, 75%, 80%, 85%, 86%, 87%, 88%, 89%, 90%, 91%, 92%, 93%, 94%, 95% or 96% methanol. If the solubility was not completed at heated temperature, an amount of methanol was added to the suspension until the complete dissolution was obtained. Then the solution was cooled at 10° C. or 5° C. and left at this temperature overnight. The time needed by cooling ramp depends on the initial temperature; the cooling ramp is applied and followed by using a thermo-cryostat equipped with a PT100 and remote control of the temperature.

The suspensions were recovered, filtered under vacuum and analyzed by XRPD.

In preferred embodiments, the crystallization was performed by using mixture of methanol/water 85:15.

Example 2: Precipitation by Anti-Solvent Addition

The DBD sample was dissolved in 2 mL of solvent to obtain an oversaturated solution at room temperature. The suspension was left under stirring overnight and then was filtered with a Whatman filter (0.45 μm) to obtain a clear solution. Examples of solvents include dimethyl formamide (DMF), dimethyl sulfoxide (DMSO). N,N-dimethylacetamide (DMA), or 1-methyl-2-pyrrolidone (MPY). The precipitation experiments were performed following two different procedures as described below:

1. Approx. 10 mL of anti-solvent was quickly added to the saturated solution under magnetic stirring at room temperature. (Direct)

2. 2 mL of saturated solution were added (about 1 drop/second) to approx. 10 mL of anti-solvent under magnetic stirring at room temperature. (Inverse)

As "Inverse" we intend the precipitation by dropping the solution of the product in the anti-solvent.

Examples of anti-solvents include Water, p-Xylene, Dichloromethane, Acetone, Acetonitrile, Ethyl Acetate, Diethyl ether, T-Butyl Methyl Ether, Toluene, Methanol and Chloroform.

The suspensions were recovered, filtered under vacuum and analyzed by XRPD.

Example 3. X-Ray Powder Diffraction of New Crystalline Polymorph

The analysis was carried out using a X'Pert PRO PANalytical. The sample was positioned on a sample holder untreated and covered with a Kapton film to isolate the sample from the atmosphere and to ensure the safety of the operator.

The X'Pert PRO X-ray diffraction system consists of the following parameters:

Ceramic Diffraction X-Ray Tubes

General Tube Specifications

| | |
|---|---|
| Focus type: | LFF (Long Fine Focus) |
| Focus dimensions: | 12 mm × 0.4 mm |
| Focus quality: | To COCIR specifications |
| Take-off angle (with no intensity loss over range) | |
| line focus: | 0°-12° (also dependent on shutter opening) |
| point focus: | 0°-20° (also dependent on shutter opening) |
| Be window diameter: | 14 mm |
| Be window thickness: | 300 μm |

Power Characteristics

| High power ceramic diffraction X-ray tube with copper anode | |
|---|---|
| Maximum power: | 2.2 kW |
| Maximum high tension: | 60 kV |

-continued

| High power ceramic diffraction X-ray tube with copper anode | |
| --- | --- |
| Maximum anode current | 55 mA |
| Advised power settings: | 80%-85% of maximum power |
| Advised standby ratings: | 30-40 kV, 10-20 mA |

Spectral Purity

| | |
| --- | --- |
| Foreign lines measured with a β-filter at 40 kV relative to the Kα line: | On delivery <1% |
| Increase per 1000 hours of tube life: | <1% for tubes with Cu anode |

Environmental Conditions

| | |
| --- | --- |
| Operating temperature: | +5° C. to +40° C. |
| Storage temperature: | −40° C. to +70° C. |
| Electrical safety: | IEC1010-1 |

Cooling Water Conditions

The cooling water used should not cause corrosions or deposit sediment in the tube. If the water is dirty or contains an unduly high concentration of salts, use of a closed cooling system employing clean, not distilled water, may be necessary.

| | |
| --- | --- |
| Quality: | Drinking water |
| Flow: | 3.5-5 l/minute |
| Maximum pressure: | 0.8 MPa |
| Pressure drop at 3.5 l/minute: | 0.2 +/− 0.04 MPa |
| Max. Temperature: | 35° C. |
| Min. Temperature: | Depends on dew point of air |

Goniometers X'Pert PRO

X'Pert PRO X-ray diffraction systems are based on the PW3065/6x Goniometer. The goniometer contains the basic axes in X-ray diffractometry: the θ and 2θ axes. PW3050/60 X'Pert PRO Standard Resolution Goniometer:

| | |
| --- | --- |
| Operation mode | Horizontal or vertical, θ-θ or θ-2θ mode |
| Reproducibility | 0.0001°0.001° (with attachments) |
| Scan speed | 0.000001-1.27°/s |
| Slew speed | 12°/s (with attachments) |
| Minimum step size | 0.001° |
| 2θ range | −40°-+220° |
| θ range | −15°-+181° |
| 2θ measurement range | Dependent on optics, geometry & sample stage |
| Diffractometer radius 130-240 mm (X'Pert PRO MPD systems); | 240 mm is standard setting |
| Distance goniometer face-diffraction plane | 150 mm |

RTMS Detector

X'Celerator:

| | |
| --- | --- |
| Used with | Line focus and point focus |
| Used in | All systems |
| Radiation type | Optimized for Cu radiation |
| 99% linearity range | 0-900 kcps overall 0-7000 cps local |
| Maximum count rate | 5000 kcps overall 250 kcps local |
| Maximum background noise | <0.1 cps |
| Typical energy resolution for Cu Kα radiation | 25% |
| Efficiency for Cu Kα | 93% |
| Detector window size | 15 mm parallel to line focus 9 mm perpendicular to line focus |
| Active length | 9 mm (2.2° at 240 mm goniometer radius; 1.6° at 320 mm goniometer radius) |
| Smallest step size | 0.0021° at 240 mm goniometer radius/0.0016° at 320 mm goniometer radius |
| Operating modes | Scanning mode |

FIG. 1 and FIG. 2 represent the results of the XRDP of the new crystalline DBD polymorph (black line) produced by the methods described in Examples 1 and 2 as compared to the calculated pattern for DBD (red line) as reported in *Acta. Cryst.* (1971) B27, 806-815. Table 1 (above) provides the values calculated.

Example 4: Differential Scanning Calorimetry (DSC)

The DSC Analyses was performed on a DSC 200 F3 Maia® using the following parameters:

| | |
|---|---|
| Temperature range: | −170° C. . . . 600° C. |
| Heating rates: | 0.001K/min . . . 100K/min |
| Cooling rates: | 0.001K/min . . . 100K/min (depending on temperature) |
| Sensor: | heat flux system |
| Measurement range | 0 mW . . . ± 600 mW |
| Temperature accuracy: | 0.1K |
| Enthalpy accuracy: | generally <1% |
| Cooling options: | Forced air (down to RT), $LN_2$ (down to −170° C.) |
| Purge gas rate: | 60 ml/min |
| Intracooler for the extended rate: | −40° . . . 600° C. |

The sample was weighed in an aluminum pan hermetically sealed with an aluminum cover. The analysis was performed heating the sample from 25° C. to 350° C. at 10K/min.

The results from the differential scanning calorimetry for the crystalline polymorphic form of DBD obtained using any of the solvents shown in Table 3 is shown in FIGS. 3 and 4. An endothermic point onset at about 184.4° C. and peak at approximately 191° C. as determined by differential scanning calorimetry was recorded.

Example 5: FT-Raman

The FT-Raman spectrum was recorded on a Thermo iS50 FT-Raman spectrometer. The sample was positioned between two glass slides. The excitation source was a $Nd^{3+}$-YAG laser (1064 nm) in the backscattering (180°) configuration. The focused laser beam diameter was about 60 μm and the spectral resolution 8 $cm^{-1}$. The spectra were recorded with a laser power at the sample of about 50 mW.

TABLE 4

| Position (cm$^{-1}$) | Intensity (a.u.) |
|---|---|
| 104 | 133.115 |
| 161 | 67.056 |
| 178 | 69.272 |
| 218 | 80.872 |
| 258 | 75.269 |
| 341 | 126.701 |
| 424 | 115.956 |
| 487 | 74.570 |
| 667 | 190.521 |
| 855 | 82.459 |
| 926 | 90.834 |
| 1030 | 82.962 |
| 1077 | 85.126 |
| 1104 | 85.791 |
| 1154 | 77.640 |
| 1248 | 91.378 |
| 1319 | 80.510 |
| 1383 | 84.104 |
| 1438 | 85.061 |
| 2856 | 73.654 |
| 2912 | 96.522 |
| 2965 | 196.591 |

TABLE 4-continued

| Position (cm$^{-1}$) | Intensity (a.u.) |
|---|---|
| 3026 | 118.035 |
| 3225 | 77.347 |
| 3407 | 75.917 |

Figure 5:
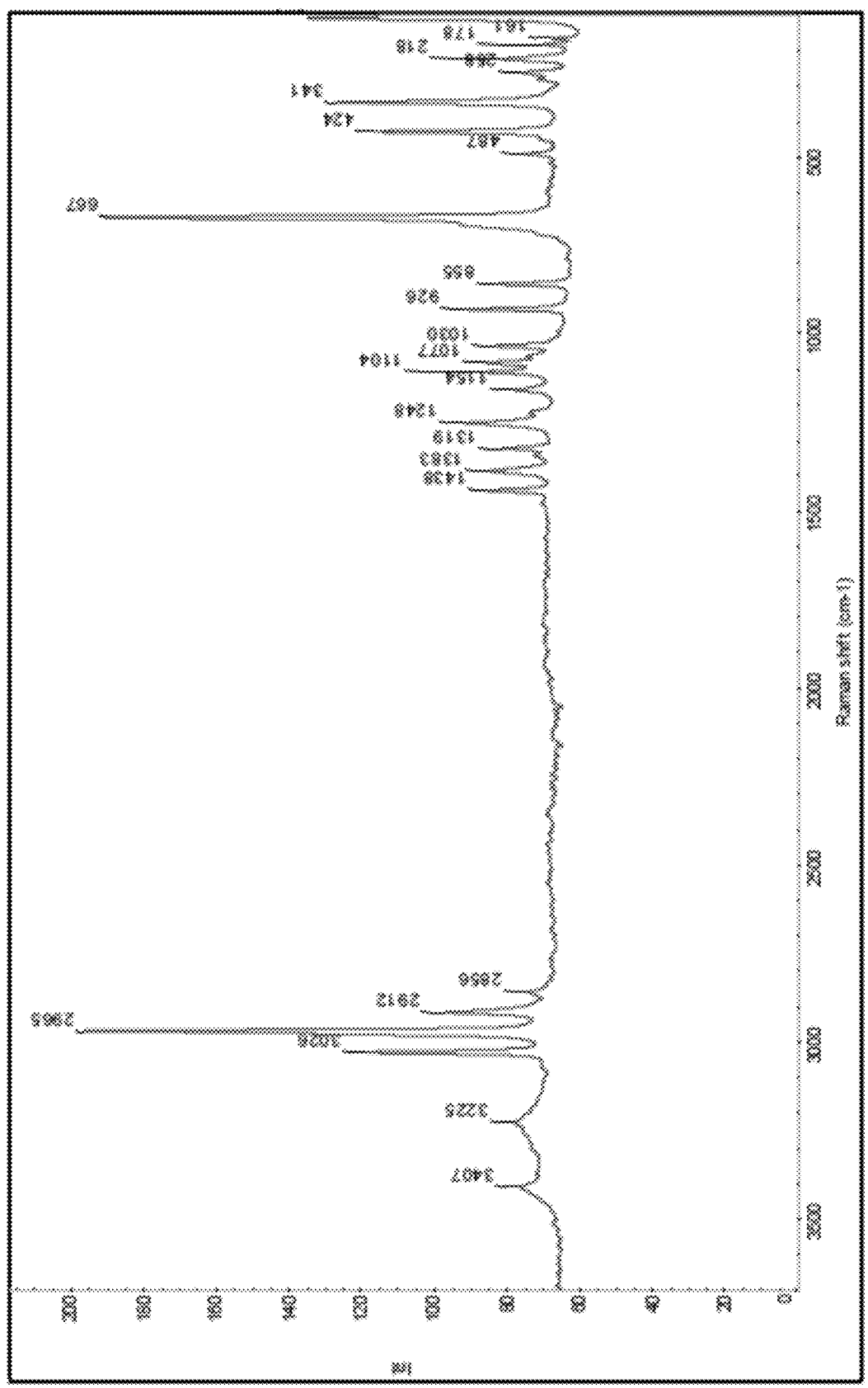
FIG. 5 represents the FT-Raman spectrum of the crystalline DBD polymorph described herein. The peak list of the FT-Raman spectrum is shown in Table 3 below.

The FT-Raman spectrum of the crystalline polymorph is shown in FIG. 5. The peak list of the FT-Raman spectrum is shown in Table 4.

Example 6: $^1$H NMR

The analysis was carried out using the Gemini Varian 400 MHz. The sample was dissolved in DMSO-d6, 8 transients with delay t1=1 sec were collected at 25° C.

Figure 6:
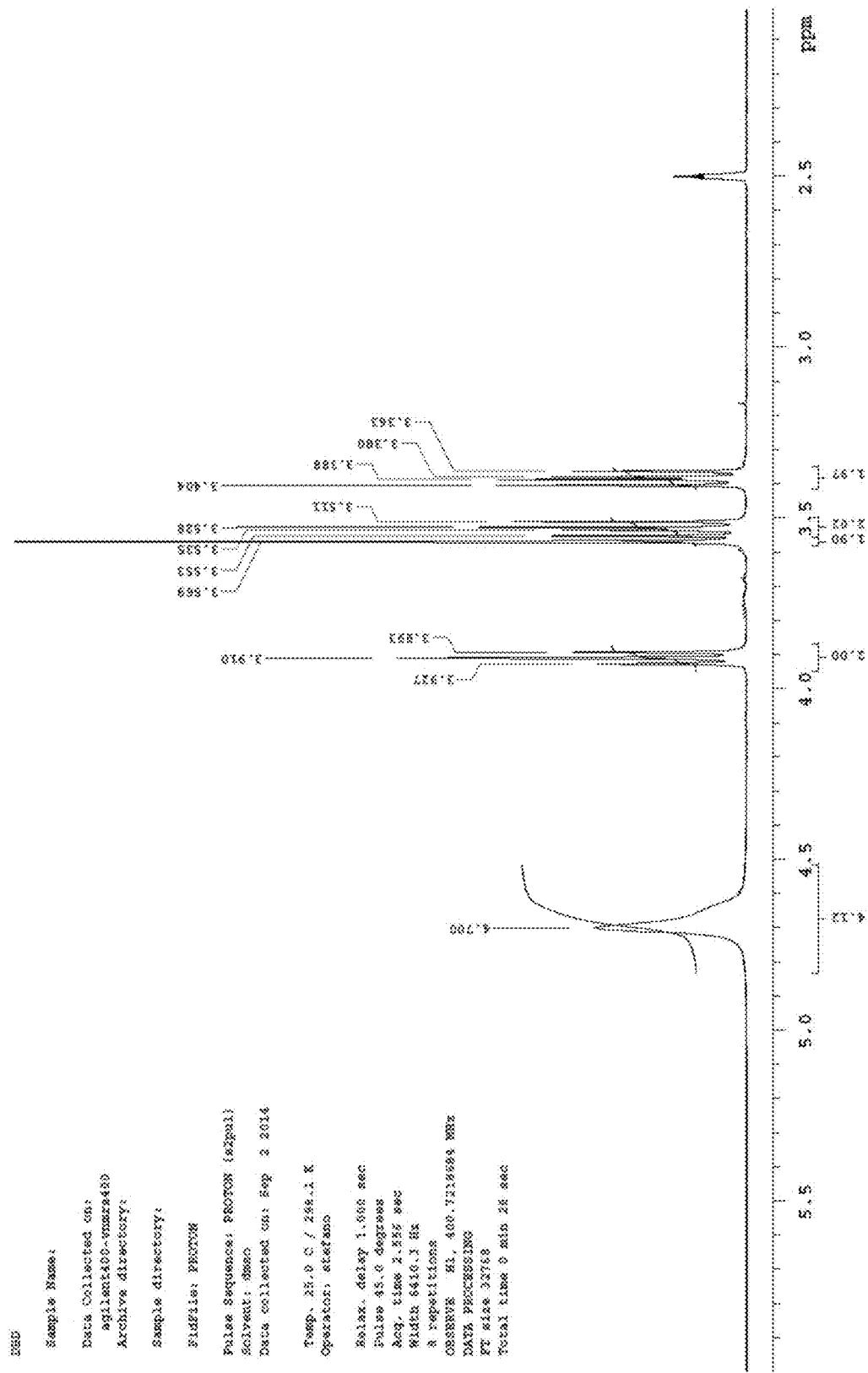
FIG. 6 represents the $^1$H NMR analysis of the crystalline DBD polymorph.

The $^1$H NMR spectrum of the crystalline polymorph is reported in FIG. 6. $^1$H-NMR (400 MHz. DMSO-$d_6$, d1=1 sec.) δ: 3.38 (2H, dd. J=6.8, 10.0 Hz), 3.53 (2H, dd, J=6.8, 10.0 Hz), 3.57 (2H, s), 3.91 (2H, t, J=6.8 Hz), 4.70 (4H, br. s).

Example 7: $^{13}$C NMR

The analysis was carried out using the Gemini Varian 400 MHz. The sample was dissolved in DMSO-d6, 464 transients with delay t1=2 sec were collected at 25° C.

Figure 7:
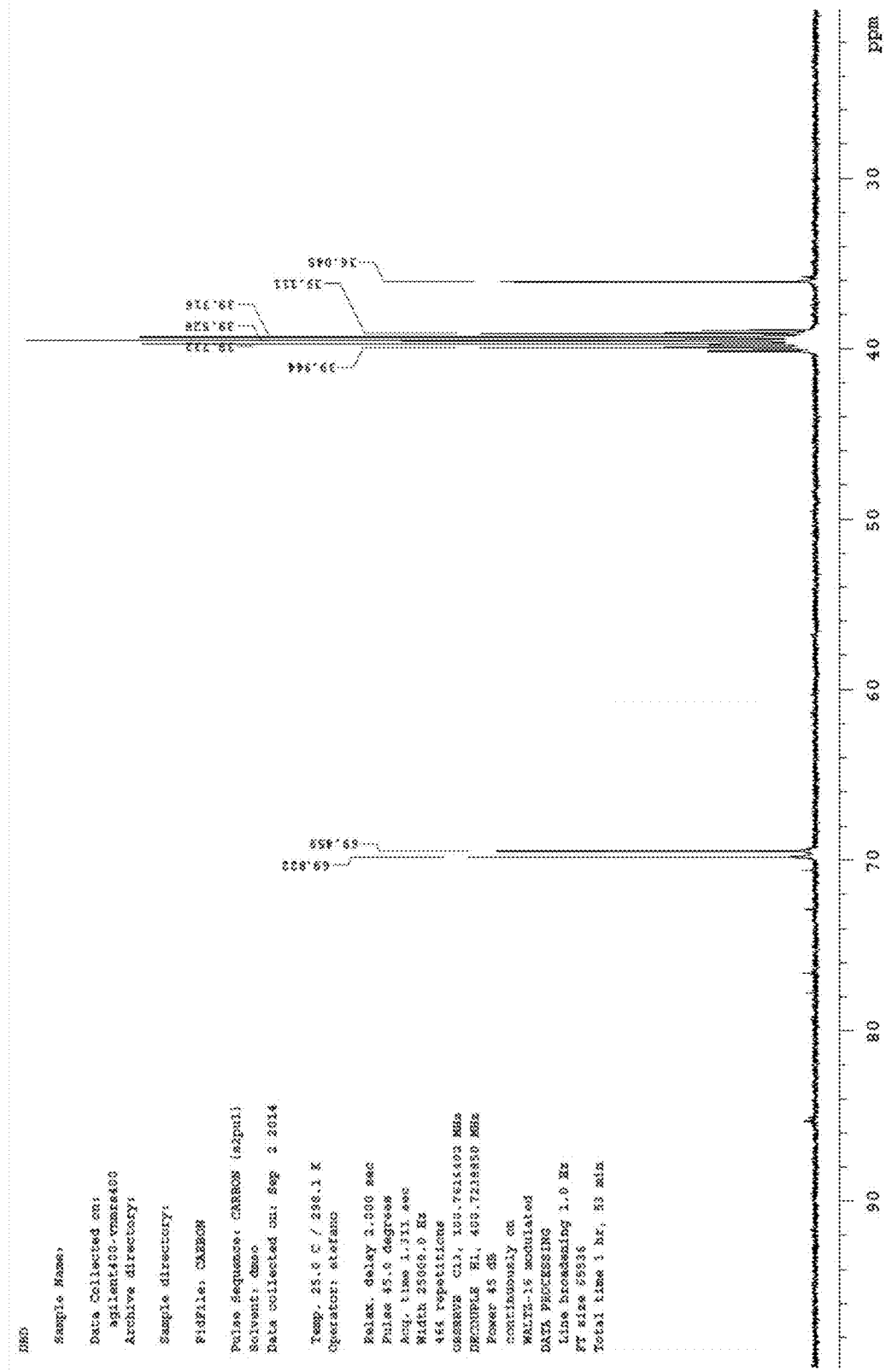
FIG. 7 represents the $^{13}$C NMR analysis of the crystalline DBD polymorph.

The $^{13}$C NMR spectrum of the sample is reported in FIG. 7. $^{13}$C NMR (100 MHz, DMSO-$d_6$, $d_1$=2 sec.) δ: 36.0 (CHOH); 69.4 (CH2Br); 69.8 (CH2Br).

Example 8: Thermogravimetric Analysis (TGA)

The analysis was carried out using the Mettler Toledo Stare System with the following parameters. The sample was weighed in an aluminum pan hermetically sealed with an aluminum pierced cover. The analysis was performed heating the sample from 25° C. to 450° C. at 10K/min.

Temperature Data

| | |
|---|---|
| Temperature range | RT . . . 1100° C. |
| Temperature accuracy | ±1K |
| Temperature precision | ±0.4K |
| Heating rate | 0.02 . . . 250K/min |
| Cooling time | 20 min (1100 . . . 100° C.) |
| Sample volume | ≤100 µL |

Special Modes

| | |
|---|---|
| Automation | 34 sample positions |
| TGA-FTIR | coupled with Thermo Nicolet 6700 spectrometer |
| Balance data | XP5 |
| Measurement range | ≤5 g |
| Resolution | 1.0 µg |
| Weighing accuracy | 0.005% |
| Weighing precision | 0.0025% |
| Internal ring weights | 2 |
| Blank curve reproducibility | better than ±10 µg over the whole temperature range |

Figure 8:
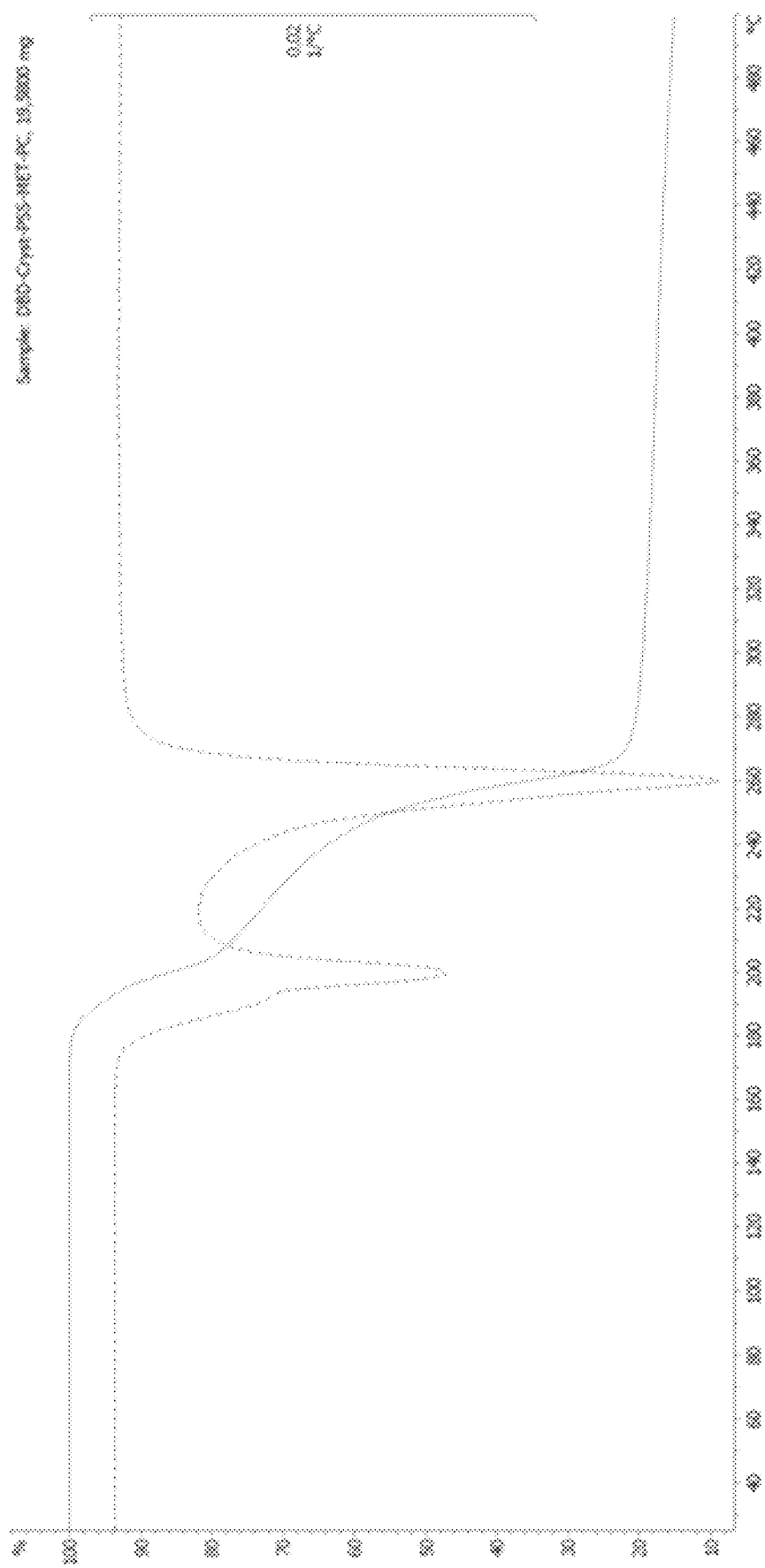
FIG. 8 represents the results from the TGA analysis of the crystalline DBD polymorph.

The TGA profile of the crystalline polymorph shows the degradation of the sample after approximately 170° C. as shown in FIG. 8.

Example 9: Stability Tests

The sample was stored in the following conditions (a) 25° C. and 60% RH for 7 days and (b) 60° C. and 75% RH for 3 days. The samples were analyzed after the test by XRPD.

Figure 9:
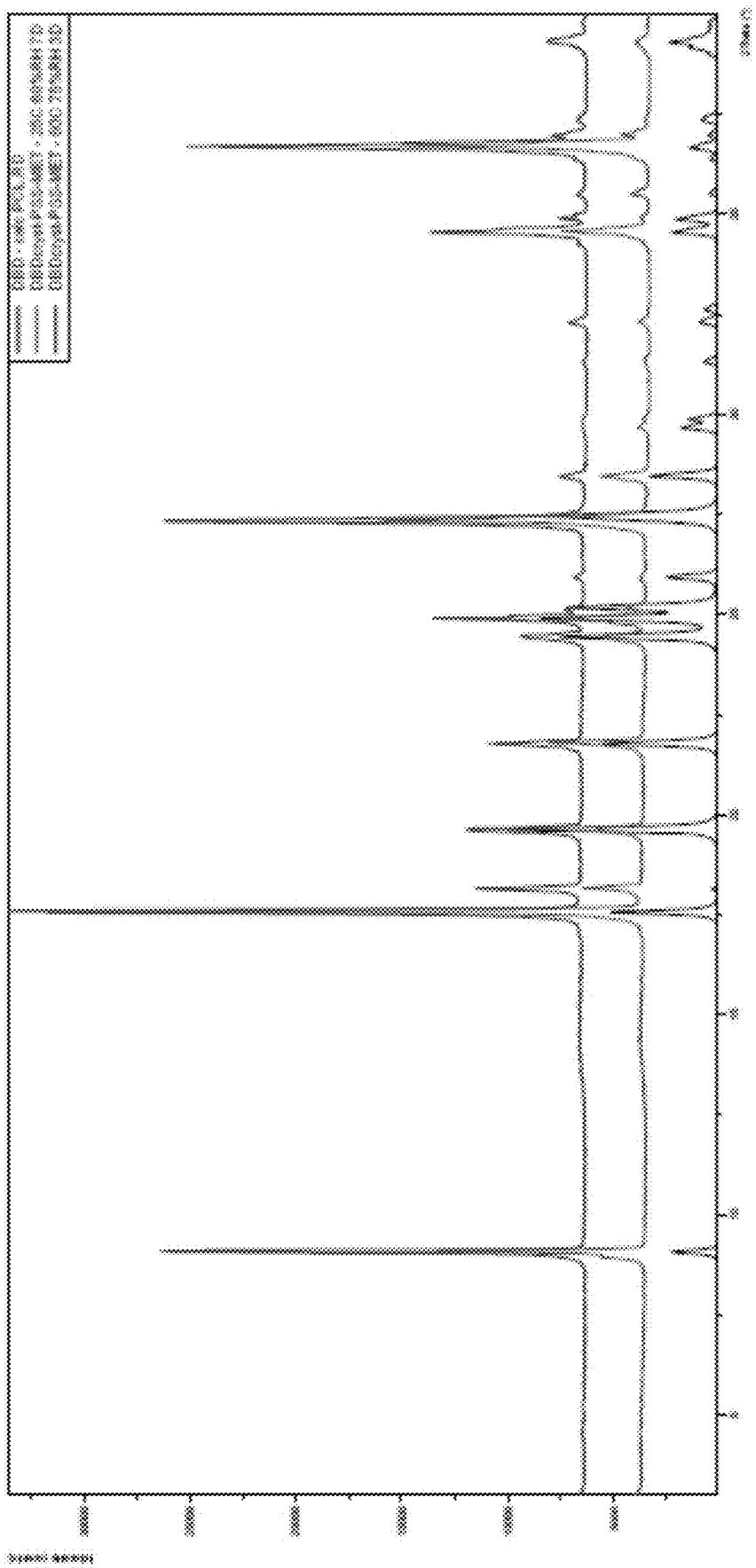
FIG. 9 represents the results from stability tests. Comparison crystalline DBD polymorph and experimental diffraction patterns of the not-ground crystalline sample obtained by slow precipitation after 7 days at 60° C. and 75% RH (red line) and after 3 days at 25° C. and 60% RH (blue line).

The crystalline polymorphic form after 7 days at 25° C. and 60% RH and after 3 days at 60° C. and 75% RH is stable as shown in FIG. 9

Example 10: Growth Inhibitory Assay

The growth inhibitory of the crystalline DBD polymorph can be studied on a variety of different growth inhibitory assays that are well known in the art. For example, different kinds of transplantable mouse, rat, rabbit and/or human tumors can be studied using the crystalline polymorph described herein. Major doses can be given in spontaneous tumors (e.g., breast cancer, leukemia) as well as in induced tumors (such as, for example, mouse skin tumor). Animal models, such as, for example, Wistar-rats and/or Swiss-, and/or $C_2$ sandy mice can be used.

For example, fragments of solid tumors to be tested measuring 1-2 mm across can be inoculated s.c. or i.m. in the animal model with a needle. Alternatively, ascities tumors can be inoculated i.p. or i.v. as suspensions of two million cells. Body weight will be measured every day.

The animals are considered cured if, for example, 60 days after inoculation with the crystalline polymorph described herein, they are free from tumor and/or if the loss in body weight does not exceed 10%.

Example 11: Predictive Profile of Crystalline DBD Polymorph Response Based on Gene Expression Analysis Gene expression analysis (including but not limited to a Whole-Genome cDNA-mediated Annealing, Selection, Extension and Ligation (DASL) assay, a genome-wide gene expression profiling method for analyzing partially degraded RNA) can be used to generate a predictive profile to identify tumor cell lines that are most likely to respond to treatment with the crystalline DBD polymorph or compositions thereof.

For example, serum free cell cultures of tumor cell lines can be treated with the crystalline DBD polymorph or compositions thereof and the resulting changes in gene expression (e.g., the untreated cell lines versus the treated cell lines) can be analyzed. Based on the outcome of the treatment (e.g., whether treatment with the DBD polymorph was effective in inhibiting cell growth) a profile (e.g., identification of specific biomarkers) for predicting which tumors are most likely to respond to treatment by the crystalline DBD polymorph or compositions thereof can be generated.

Examples of generating predictive profiles may be found in Pont et al., "The Bcl-2 inhibitor Obatoclax overcomes resistance to histone deacetylase inhibitors SAHA and LBH589 as radiosensitizers in patient-derived glioblastoma stem-like cells". Genes & Cancer, vol. 5 (2014), which is incorporated herein by reference in its entirety, and Balvers et al., "Serum-free culture success of glial tumors is related to specific molecular profiles and expression of extracellular matrix-associated gene modules" Neuro-Oncol., vol. 15, pp. 1684 (2013) which is also incorporated by reference herein in its entirety. For example, based on these techniques, a set of genes may be identified to predict the clinical outcome of treatment with a particular therapeutic or combination of therapeutics. Additionally, such techniques may be used to identify functional pathways targeted by a particular therapeutic, such as by the crystalline DBD polymorph, and to potentially elucidate corresponding mechanisms of action of a particular therapeutic.

The IC50 (inhibitory concentration of drug resulting in 50% viability) value can be used to compare differing doses of the crystalline DBD polymorph, as well as combinations thereof with other chemical, radiation and chemotherapeutic moieties, e.g., to establish an optimal treatment regime.

What is claimed:

1. A crystalline polymorph of 1,6-dibromo-1,6-dideoxy-dulcitol (DBD), wherein the crystalline polymorph exhibits an X-Ray Powder Diffraction Pattern substantially the same as the X-Ray Powder Diffraction Pattern shown in FIG. 1 and/or FIG. 2 and where said crystalline polymorph is formulated with at least one pharmaceutically acceptable carrier.

2. The crystalline polymorph of claim 1, wherein said crystalline polymorph is characterized by:
   a. at least two peaks selected from 19.59° (100,00), 24.380° (79,52), 31.260° (8,32), 34.500° (25,56) and 34.810° (22,83), 39.260° (23,63) at 2θ±0.1°;
   b. at least three peaks selected from 19.59° (100,00) and 24.380° (79,52), 31.260° (8,32), 34.500° (25,56), 34.810° (22,83), and 39.260 (23,63) at 2θ±0.1°;
   c. at least four peaks selected from 19.59° (100,00), 24.380° (79,52), 31.260° (8,32), 34.500° (25,56), 34.810° (22,83), and 39.260° (23,63) at 2θ±0.1°; or
   d. at least five peaks selected from 19.59° (100,00), 24.380° (79,52), 31.260° (8,32), 34.500° (25,56), 34.810° (22,83), and 39.260° (23,63) at 2θ±0.1°; or
   e. peaks at 19.59° (100,00), 24.380° (79,52), 31.260° (8,32), 34.500° (25,56), 34.810° (22,83), and 39.260° (23,63) at 2θ±0.1°.

3. The crystalline polymorph of claim 1, wherein the crystalline polymorph exhibits an X-Ray Powder Diffraction Pattern substantially the same as the X-Ray Powder Diffraction Pattern described in Table 1.

4. The crystalline polymorph of claim 1, wherein the crystalline polymorph exhibits a beta angle of 96°.

5. The crystalline polymorph of claim 1, wherein the crystalline polymorph exhibits an endothermic point onset at about 184.4° C. and peak at approximately 191° C. as determined by differential scanning calorimetry.

6. The crystalline polymorph of claim 1, wherein the crystalline polymorph is characterized by a differential scanning calorimetry pattern substantially the same as the differential scanning calorimetry pattern shown in FIG. 3 and/or FIG. 4.

7. The crystalline polymorph of claim 1, wherein the crystalline polymorph is characterized by a FT-Raman spectrum as shown in Table 3.

8. A method of making the crystalline polymorph of claim 1, wherein the method comprises:
   a. Resuspending DBD in a solution comprising a solvent, wherein the solvent comprises methanol, dimethyl formamide (DMF), dimethyl sulfoxide (DMSO), N,N-dimethylacetamide (DMA), or 1-methyl-2-pyrrolidone;
   b. Heating the solution; and
   c. Precipitating the crystalline polymorph from the solution.

9. The method of claim 8, wherein the solvent comprises methanol.

10. The method of claim 9, wherein the solvent comprises a mixture of water and methanol.

11. The method of claim 10, wherein the mixture comprises 70%, 75%, 80%, 85%, 86%, 87%, 88%, 89%, 90%, 91%, 92%, 93%, 94%, 95% or 96% methanol.

12. The method of claim 8, wherein the solution is heated to 65° C.

13. The method of claim 8, wherein the solution is cooled to 5° C.

14. The method of claim 8, wherein the solution is cooled at a rate of 0.5° C./min.

15. The method of claim 8, wherein the crystalline polymorph is precipitated using an anti-solvent.

16. The method of claim 15, wherein the antisolvent is selected from Water, p-Xylene, Dichloromethane, Acetone, Acetonitrile, Ethyl Acetate, Diethyl ether, T-Butyl Methyl Ether, Methanol, Toluene and Chloroform.

17. The crystalline polymorph produced by the method claim 8.

18. A pharmaceutical composition comprising the crystalline polymorph of claim 1.

19. The pharmaceutical composition of claim 18, wherein the crystalline polymorph is formulated with polyethylene glycol (PEG).

20. The pharmaceutical composition of claim 19, wherein the crystalline polymorph is covalently linked to one or more molecules of PEG.

21. The pharmaceutical composition claim 18, further comprising a molecule which inhibits cellular DNA-repair mechanisms.

22. The pharmaceutical composition of claim 21, wherein the molecule is a polyADP-ribose polymerase protein (PARP) inhibitor.

23. The pharmaceutical composition of claim 21, wherein the molecule is an alkylating agent.

24. The pharmaceutical composition of claim 18, further comprising a chemotherapeutic agent.

25. A method of treating a patient suffering from cancer, wherein the method comprises administering to a patient an effective amount of the crystalline polymorph of claim 1.

26. The method of claim 25, wherein the patient is suffering from cancer selected from: adenocarcinoma, sarcoma, skin cancer, melanoma, bladder cancer, brain cancer, breast cancer, uterine cancer, ovarian cancer, prostate cancer, lung cancer, colorectal cancer, cervical cancer, liver cancer, head and neck cancer, esophageal cancer, pancreas cancer, pancreatic ductal adenocarcinoma (PDA), renal cancer, stomach cancer, multiple myeloma, cerebral cancer, lymphoma, melanoma, cancers of the central nervous system, pediatric cancers, pediatric brain cancer, pediatric leukemia, non-small cell lung cancer, gastric cancer, ovarian cancer, or uterine cancer.

27. The method of claim 25, wherein the cancer is a metastatic cancer.

28. The method of claim 27, wherein the metastatic cancer has metastasized to the brain.

29. The method of claim 25, wherein the crystalline polymorph is administered in combination with radiation therapy.

30. The method of claim 29, wherein the radiation therapy is administered simultaneously, sequentially, or separately with the crystalline polymorph.

31. The method of claim 25, wherein the method of treating a patient further comprises using gene expression analysis to generate a predictive profile to identify patients most likely to respond to treatment with the crystalline polymorph or the pharmaceutical compositions thereof.

* * * * *